(12) United States Patent
Demuth et al.

(10) Patent No.: US 6,890,905 B2
(45) Date of Patent: *May 10, 2005

(54) METHODS FOR IMPROVING ISLET SIGNALING IN DIABETES MELLITUS AND FOR ITS PREVENTION

(75) Inventors: Hans-Ulrich Demuth, Halle/Saale (DE); Konrad Glund, Halle/Saale (DE); Andrew J. Pospisilik, West Vancouver (CA); Kerstin Kuehn-Wache, Halle/Saale (DE)

(73) Assignee: Prosidion Limited, Oxford (GB)

(*) Notice: Subject to any disclaimer, the term of this patent is extended or adjusted under 35 U.S.C. 154(b) by 52 days.

This patent is subject to a terminal disclaimer.

(21) Appl. No.: 10/216,349

(22) Filed: Aug. 9, 2002

(65) Prior Publication Data

US 2003/0119736 A1 Jun. 26, 2003

Related U.S. Application Data

(63) Continuation-in-part of application No. 09/824,622, filed on Apr. 2, 2001, now Pat. No. 6,500,804.

(51) Int. Cl.[7] .................. A61K 38/00; A61K 31/70; A61K 31/425
(52) U.S. Cl. ................. 514/19; 514/23; 514/365
(58) Field of Search ................. 514/19, 365, 23

(56) References Cited

U.S. PATENT DOCUMENTS

| | | | |
|---|---|---|---|
| 2,961,377 A | 11/1960 | Shapiro et al. | 167/65 |
| 3,174,901 A | 3/1965 | Sterne | 167/65 |
| 3,879,541 A | 4/1975 | Kabbe et al. | 424/326 |
| 3,960,949 A | 6/1976 | Ahrens et al. | 260/564 B |
| 4,028,402 A | 6/1977 | Fischer et al. | 260/501.14 |
| 4,935,493 A | 6/1990 | Bachovchin et al. | 530/331 |
| 5,433,955 A | 7/1995 | Bredehorst et al. | 424/94.3 |
| 5,462,928 A | 10/1995 | Bachovchin et al. | 514/19 |
| 5,512,549 A | 4/1996 | Chen et al. | 514/12 |
| 5,543,396 A | 8/1996 | Powers et al. | 514/19 |
| 5,614,379 A | 3/1997 | MacKellar | 435/68.1 |
| 5,624,894 A | 4/1997 | Bodor | 514/2 |
| 5,939,560 A | 8/1999 | Jenkins et al. | 548/535 |
| 6,006,753 A | 12/1999 | Efendic | 128/898 |
| 6,011,155 A * | 1/2000 | Villhauer | 544/333 |
| 6,107,317 A * | 8/2000 | Villhauer | 514/365 |
| 6,110,949 A * | 8/2000 | Villhauer | 514/365 |
| 6,124,305 A * | 9/2000 | Villhauer | 514/272 |
| 6,172,081 B1 * | 1/2001 | Damon | 514/307 |
| 6,303,661 B1 * | 10/2001 | Demuth et al. | 514/866 |
| 6,319,893 B1 * | 11/2001 | Demuth et al. | 514/2 |
| 6,500,804 B2 * | 12/2002 | Demuth et al. | 514/19 |

FOREIGN PATENT DOCUMENTS

| | | | | |
|---|---|---|---|---|
| DD | DD 296 075 A5 | 11/1991 | | C07D/295/04 |
| DE | 25 42 598 A1 | 4/1976 | | C07C/129/16 |
| DE | 196 16 486 C2 | 10/1997 | | A61K/45/00 |
| DE | 299 09 210 U | 9/1999 | | A61K/31/425 |
| DE | 198 26 972 A1 | 12/1999 | | A61K/38/05 |
| EP | 0 658 568 A1 | 6/1995 | | C07K/14/605 |
| EP | 0 708 179 A2 | 4/1996 | | C12N/15/16 |
| EP | 0 995 440 A1 | 4/2000 | | A61K/31/425 |
| FR | 2 085 665 | 12/1971 | | A61K/27/00 |
| FR | 2 696 740 A1 | 4/1994 | | C07D/207/404 |
| JP | 04-288098 | 10/1992 | | A61K/37/64 |
| JP | 4334357 | 11/1992 | | C07C/233/57 |
| WO | WO 91/11457 | 8/1991 | | C07K/7/34 |
| WO | WO 91/16339 | 10/1991 | | C07K/5/10 |
| WO | WO 91/17767 | 11/1991 | | A61K/37/54 |
| WO | WO 93/08259 | 4/1993 | | |
| WO | WO 95/11689 | 5/1995 | | A61K/37/00 |
| WO | WO 95/15309 | 6/1995 | | C07D/207/16 |
| WO | WO 95/29691 | 11/1995 | | A61K/38/00 |
| WO | WO 97/40832 | 11/1997 | | A61K/31/425 |
| WO | WO 97/45117 | 12/1997 | | A61K/31/435 |
| WO | WO 98/19998 | 5/1998 | | C07D/207/00 |
| WO | WO 98/22494 | 5/1998 | | C07K/5/06 |
| WO | WO 99/46272 A | 9/1999 | | C07F/9/572 |
| WO | WO 99/62914 | 12/1999 | | C07F/5/02 |
| WO | WO 00/01849 | 1/2000 | | C12Q/1/68 |
| WO | WO 00/10549 | 3/2000 | | A61K/31/00 |
| WO | WO 00/53171 | 9/2000 | | A61K/31/155 |
| WO | WO 01/74299 A2 | 10/2000 | | |
| WO | WO 01/34594 A1 | 5/2001 | | C07D/401/06 |
| WO | WO 01/62266 A2 | 8/2001 | | A61K/38/00 |
| WO | WO 01/89569 A1 | 11/2001 | | A61K/45/06 |
| WO | WO 01/97808 | 12/2001 | | A61K/31/425 |
| WO | WO 02/20825 A1 | 3/2002 | | C12Q/1/00 |

OTHER PUBLICATIONS

Holst et al., "Inhibition of the Activity of Dipeptidyl–Peptidase IV as a Treatment for Type 2 Diabetes", Diabetes (1998), 47(11), pp. 1663–1670.*

Campbell, I.W. *New Antidiabetic Drugs,* ed. C.J. Bailey & P.R. Flatt, Smith–Gordon, "Sulphonylureas and the metformin: efficacy and inadequacy". 3:33–51 (1990).

The Merck Index, 11th Edition, *An Encyclopedia of Chemicals, Drugs,* and Biologicals, 1989, p. 934.

The Merck Index, 12th Edition, *An Encyclopedia of Chemicals, Drugs,* and Biologicals, 1996, p. 1014.

*Martindale The Extra Pharmacopoeia,* 30th Edition, London Pharmaceutical Press, 1993, p. 1619.

(Continued)

*Primary Examiner*—Kevin E. Weddington
(74) *Attorney, Agent, or Firm*—Brown, Rudnick, Berlack & Israels, LLP.

(57) ABSTRACT

The present invention discloses methods for therapeutically treating mammals, including but not limited to humans, to increase the relative insulin producing performance of endogenous pancreatic β-cells, to cause differentiation of pancreatic epithelial cells into insulin producing β-cells, to improve muscle sensitivity to insulin and other weight control efforts by the chronic oral administration of a DP IV-inhibitor. The administration causes the active form of GLP-1 and other non-nutrient stimulated growth hormones to remain biologically active longer under physiological conditions. The extended presence of such hormones, in particular in the pancreatic tissue can also facilitate differentiation and regeneration of the β-cells already present that are in need of repair.

11 Claims, 16 Drawing Sheets

U.S. PATENT DOCUMENTS

*Martindale The Extra Pharmacopoeia*, 30$^{th}$ Edition, London Pharmaceutical Press, 1993, p. 36.

*Chemical Abstracts,* vol. 115. No. 15, Oct. 14, 1991 Columbus, Ohio, US; abstract No. 149947q, Schoen Ekkehard et al: "Dipeptidyl peptidase IV in the immune system. Effects of specific enzyme inhibitors on activity of dipeptidyl peptidase IV and proliferation of human lymphocytes".

*Chemical Abstracts,* vol. 126, No. 2, Jan. 13, 1997 Columbus, Ohio, US; abstract No. 16161j, Stoeckel A. et al.: "Competitive inhibition of proline specific enzymes by amino acid thioxopyrrolidides and thiazolidides".

*Chemical Abstracts,* vol. 118, No. 25, Jun. 21, 1993 Columbus, Ohio, US; abstract No. 255342k, Hosoda, et al, "Preparation of N–(heterocyclic Carbonyl) Amino Acids and Analogs as Prolyl Endopeptidase Inhibitors", (Nov. 29, 1992).

Arai et al., "Synthesis of prolyl endopeptidase inhibitors and evaluation of their structure–activity relationships: in vitro inhibition of prolyl endopeptidase from Canine Brain" *Chemical and Pharmaceutical Bulletin,* Bd. 41, No. 9, 1993, pp. 1583–1588.

J. Lin et al.: "Inhibition of depeptidyl peptidase IV by fluoroolefin–containing n–peptidyl–O–hydroxylamine peptidomimetics" *Proceedings of the National Academy of Sciences of USA,* vol. 95, Nov. 1998, pp. 14020–14024.

Korom, S., et al "Inhibition of CD26/dipeptidyl peptidase IV activity in vivo prolongs cardiac allograft survival in rat recipients", *Transplantation,* vol. 63, 1495–1500 No. 10 (1997).

Tanka, S., et al., "Suppression of arthritis by the inhibitors of dipeptidyl peptidase IV". *Int. J. Immunopharmacol,* vol. 19, No. 1, pp. 15–24, (1997).

Mentlein, R., et al., "Proteolytic processing of neuropeptide Y and peptide YY by dipeptidyl peptidase IV". *Regul. Pept.* 49, 133–144 (1993).

Wetzel, W., et al., "Effects of the CLIP fragment ACTH 20–24 on the duration of REM sleep episodes". *Neuropeptides,* 31, 41–45 (1997).

Amasheh, S., et al., "Electrophysiological analysis of the function of the mammalian renal peptide transporter expressed in *Xenopus laevis* oocytes". *J. Physiol.* 504, 169–174 (1997).

Durinx, C.; et al.; "Reference Values for Plasma Dipeptidyl–Peptidase IV activity and their Association with Other Laboratory Parameters". *Clin Chem Lab Med 2001,* Feb.; 39(2):155–9, 1 page.

Gossrau, R.; "Cytochemistry of Membrane Proteases". *Histochem J,* Jul. 1985; 17 (7):737–71, 1 page.

Hahn, T.; et al.; "Enzyme Histochemical Evidence for the Presence of Potential Blood Pressure Regulating Proteases in Cultured Villous Explants from Human First Trimester Placentae". *Acta Histochem* Dec., 1993, 95 (2):185–92, 1 page.

Heymann, E. et al., "Has Dipeptidyl Peptidase IV an Effect on Blood Pressure and Coagulation." *Klin Wochenschr,* Jan. 2, 1984;62 (1):2–10, 1 page.

Magyar, C.E. et al., "Proximal Tubule Na Transporter Responses are the same during Acute and Chronic Hypertension." *Am J. Physiol Renal Physiol,* Aug., 2000; 279 (2):F358–69, 1 page.

Papies, B. et al., "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." *Cor Vasa,* 1991; 33(3):218–26, 1 page.

Qureshi. N.U.; et al., "Endogenous Neuropeptide Y Mediates Vasoconstriction during Endotoxic and Hemorrhagic Shock". *Regul Pept,* Sep. 25, 1998; 75–76:215–20, 1 page.

Index Nominum, *International Drug Directory 1992/1993,* Medpharm Scientific Publishers, pp. 728–729.

The Merck Index, *An Encyclopedia of Chemicals and Drugs,* 9$^{th}$ Edition, Merck & Co., Inc., 1976, p. 773.

Willms et al., *Journal of Clinical Endocrinology Metabolism,* "Gastric Emptying, Glucose Responses, and Insulin Secretion after a Liquid Test Meal: Effects of Exogenous Glucagon–Like Peptide–1 (GLP–1)–(7–36) Amide in Type 2 (Noninsulin–Dependent) Diabetic Patients", 1996, 81(1): 327–332.

Hoffmann et al., *Journal of Chromatography A,* "Inhibition of dipeptidyl peptidase IV (DP IV) by anti–DP IV antibodies and non–substrate X–X–Pro– oligopeptides ascertained by capillary electrophoresis", 1995, 716:355–362.

C.B. Welch, *Medical Management of Non–Insulin–Dependent (Type II) Diabetes,* 3$^{rd}$ edition, American Diabetes Association, "Diagnosis and Classification" p. 3, 1994, Pharmacologic Intervention (2 pages).

Mannucci et al., *Diabetes Carre,* "Effect of Metformin on Glucagon–Like Peptide 1 (GLP–1) and Leptin Levels in Obese Nondiabetic Subjects", 24(3): 489–494, Mar. 2001.

Stryer, *Biochemistry* 3$^{rd\ d.,}$ "Protein Conformation, Dynamics, and Functions", 1988, p 191–193.

Pauly et al., *Regulatory Peptides,* "Abstracts Issue: Abstracts from the 11$^{th}$ International Symposium on Regulatory Peptides", Jul. 15, 1996, 64(1–3): 148 plus cover.

Gutniak et al., *New England Journal of Medicine,* "Antidiabetogenic Effect of Glucagon–like peptide–1 (7–36) Amide in Normal Subjects and Patients With Diabetes Mellitus", 1992, 326: 1316–1322.

Hendrick et al., *Metabolism—Clinical and Experimental,* "Glucagon–like Peptide–I–(7–37) Suppresses Hyperglycemia in Rats", Jan. 1993, 42(1): 1–6.

Nauck et al., *Diabetologia,* "Normalization of fasting hyperglycaemia by exogenous glucagon–like peptide 1 (7–36 amide) in Type 2 (non–insulin–dependent) diabetic patients", (1993), 36: 741–744.

Gutniak et al., *Diabetes Care,* "Subcutaneous Injectin of the Incretin Hormone Glucagon–Like Peptide 1 Abolishes Posprandial Glycemia in NIDDM", Sep. 1994, 17(9): 1039–1044.

Deacon et al., *Journal of Clinical Endocrinology and Metabolism,* "Degradation of Glucagon–Like Peptide–1 by Human Plasma in Vitro Yields and N–Terminally Truncated Peptide That Is a Major Endogenous Metabolite in Vivo", (1995), 80(3): 952–957.

H.A. Smith et al., *Veterinary Pathology* (fourth edition), "Diseases and Disorders of Metabolism: Deficiency Diseases", (1972), p 1018–1020.

G.G. Duncan, *Diseases of Metabolism (Asian edition),* "Diabetes Mellitus", (1966), p 951–957.

T.J. Kieffer et al., "Degradation of Glucose–Dependent Insulinotropic Polypeptide and Truncated Glucagon–Like Peptide 1 In Vitro and In Vivo by DP IV", *Endocrinology,* vol. 136(8), (1995), p 3585–3596.

C.F. Deacon et al., *Diabetes*, "Both Subcutaneously and Intravenously Administered Glucagon–Like Peptide I Are Rapidly Degraded from the $NH_2$–Terminus in Type II Diabetic Patients and in Healthy Subjects", Sep. 1995; 44: 1126–1131.

Pauly et al., *Metabolism*, "Improved Glucose Tolerance in Rats Treated with Dipeptidyl Peptidase IV (CD26) Inhibitor Ile–Thiazolidide", (1999), 48(3): 385–389.

*Vidal*, (1993), 69th Edition, p. 612–613.

*Goodman & Gilman's The Pharmacological Basis of Therapeutics*, Ninth Edition, (1996), p. 1510.

Nathan et al., *Diabetes Care*, "Insulinotropic Action of Glucagonlike Peptide–1–(7–37) in Diabetic and Nondiabetic Subjects", Feb. 1992, 15(2): 270–275.

*Pschyrembel*, Kininisches Wörterbuch 257, Auflage, (1994), 9 pages.

Frohman et al., *Journal of Clin. Invest.*, "Rapid Enzymatic Degradation of Growth Hormone–releasing Hormone by Plasma in Vitro and in Vivo to a Biologically Inactive Product Cleaved at the $NH_2$ Terminus", vol. 78, Oct. 1986, p 906–913.

Snow et al., *Advances In Medicinal Chemistry*, "Boronic Acid Inhibitors of Dipeptidyl Peptidase IV: A New Class of Immunosuppressive Agents", vol. 3, (1995), p 149–177.

Thorens et al., *Diabetes*, "Glucagon–Like Pepetide–I and the Control of Insulin Secretion in the Normal State and in NIDDM", (1993), 42:1219–1225.

Wakselman et al., "Inhibition of HIV–1 infection of CD 26[+] but not CD 26[−] cells by a potent cyclopeptidic inhibitor of the DPP IV activity of CD26", Abstract P 44 of the 24th *European Peptide Symposium*, (1996).

Ashworth et al., *Bioorg. Med. Chem. Lett.*, "2–Cyanopyrrolidides as Potent, Stable Inhibitors of Dipeptidyl Peptidase IV", (1996), 6(10): 1163–1166.

Endroczi et al., *Acta Physiol. Hung.*, "Dipeptidyl peptidase IV (DP–IV) and Superoxide Dismutase Activity in Thymus–Derived Lymphocytes: Effects of Inhibitory Peptides and $Zn^{2+}$ in Vitro", (1990), 75(1): 35–44.

Lee, H.S. et al., "Cathepsin B Inhibitory Peptides Derived from β–Casein," *Peptides* 21 (2000) 807–809.

Edwards, J.V. et al., *J. Peptide Res.*, "Synthesis and Activity of $NH_2$ –and COOH–Terminal Elastase Recognition Sequences on Cotton," (1999), 54: 536–543.

Wettstein, J.G. et al. *Pharmacology & Therapeutics*, "Central Nervous System Pharmacology of Neuropeptide Y.", (1995), 65(3): 397–414.

Badia–Elder N.E. et al., *Alcoholism Clinical and Experimental Research*, "Effects of Neuropeptide Y (NPY) on Ethanol Intake and Anxiety in High and Low Alcohol Drinking (HAD1/LAD1) Rats", (2000), 24(5): 82A.

Munglani R. et al., Drugs, *Adis International Ltd*, At, "The Therapeutic Potential of Neuropeptide Y Analgesic, Anxiolytic and Antihypertensive", (1996) 52(3): 371–389.

Reinhold, D. et al., *Journal of Neuroimmunology*, "Inhibitors of Dipeptidyl Peptidase IV/CD26 Suppress Activation of Human MBP–Specific CD4 + T Cell Clones", (1998) 87: 203–209.

Stöckel–Maschek, A., et al., *Biochimica et Biophysica Acta*, "Thioxo Amino Acid Pyrrolidides and Thiazolidides: new Inhibitors of Proline Specific Peptidases", (2000) 1479: 15–31.

\* cited by examiner

Fig. 6
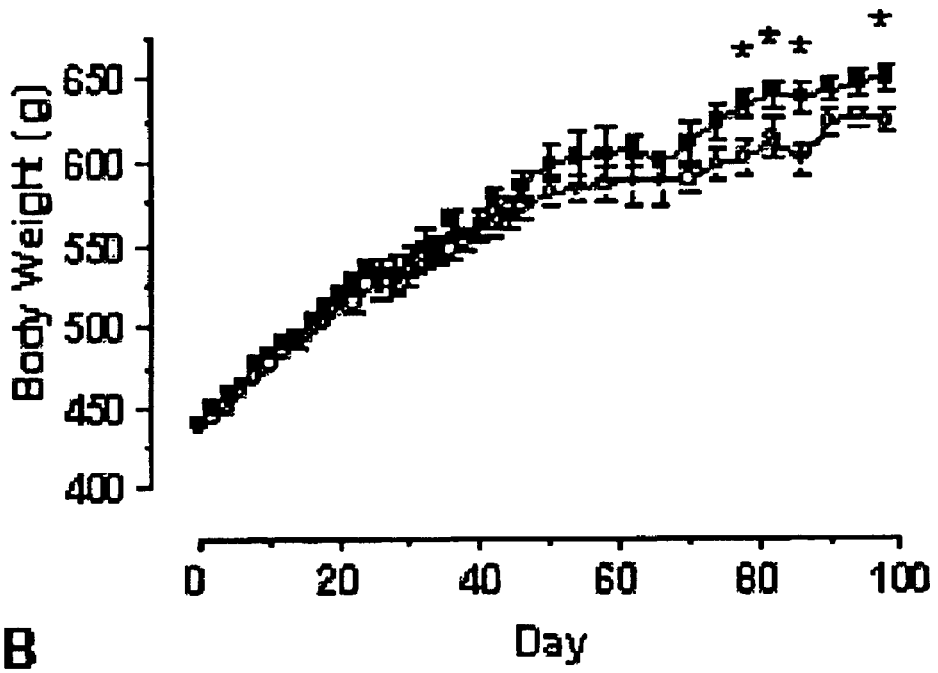
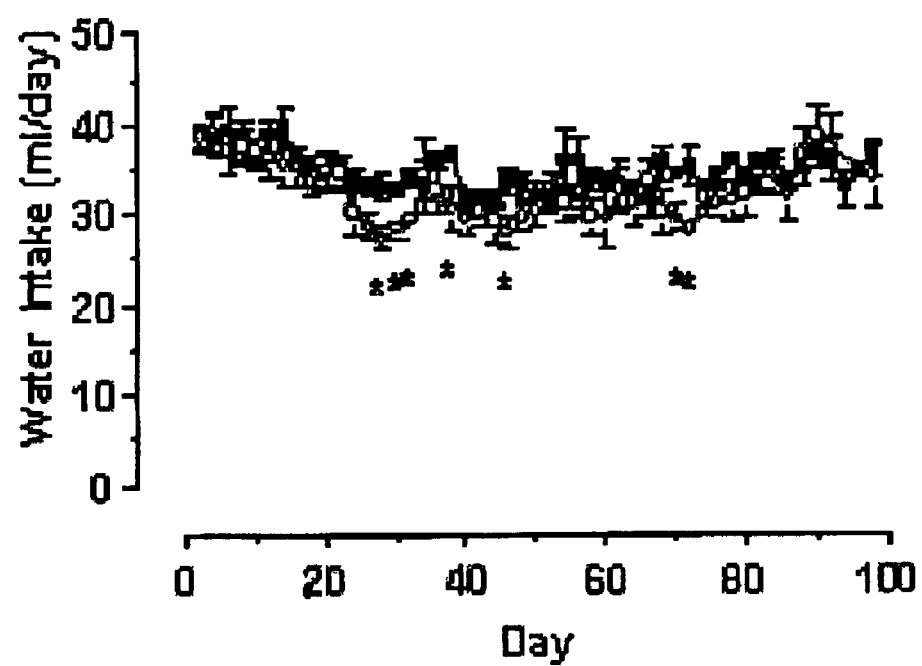

Fig. 11
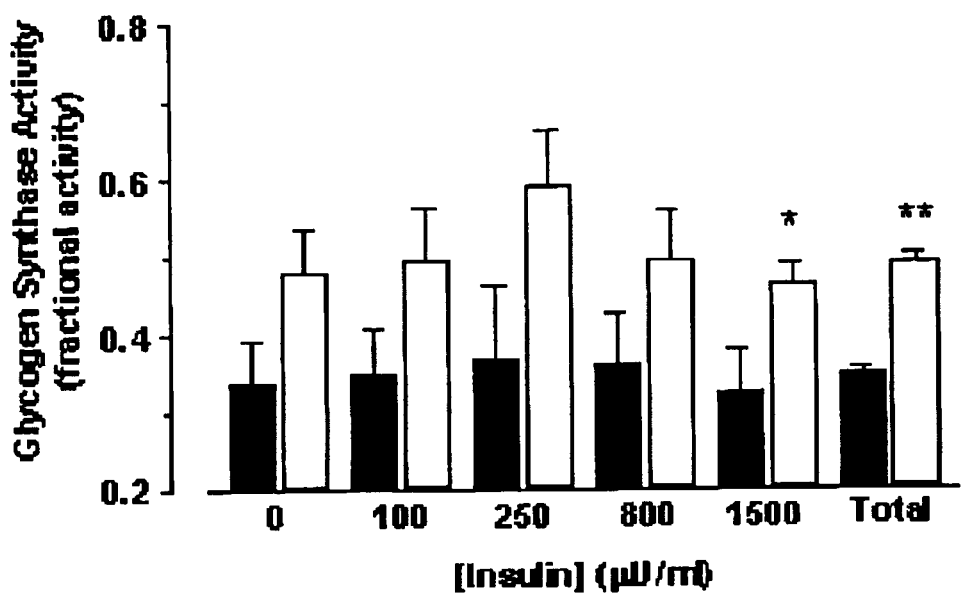
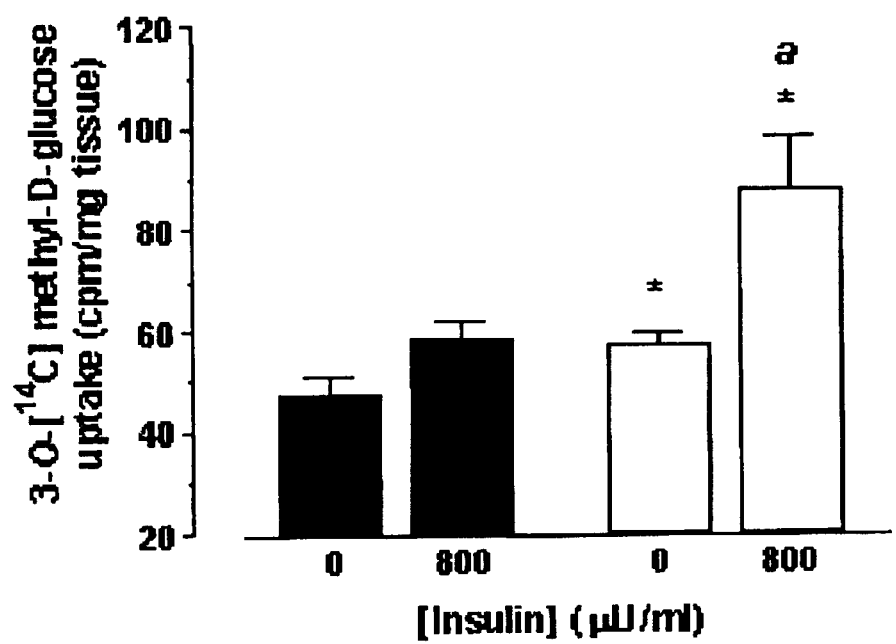

METHODS FOR IMPROVING ISLET SIGNALING IN DIABETES MELLITUS AND FOR ITS PREVENTION

CROSS REFERENCES TO RELATED APPLICATIONS

This application is a continuation-in-part application of U.S. patent application Ser. No. 09/824,622, filed Apr. 2, 2001 now U.S. Pat. No. 6,500,804.

BACKGROUND

The pancreas comprises two glandular tissues, one, is a collection of cells that form the exocrine function of the pancreas where these exocrine cells synthesize and release digestive enzymes into the intestine; the second tissue comprises the endocrine function of the pancreas which synthesize and release hormones into the circulation. Of prime importance in the endocrine function of the pancreas, are the β-cells. These cells synthesize and secrete the hormone insulin. The hormone insulin plays a vital role in maintaining normal physiological glycaemic levels. There are molecules that are effectors of the endocrine cells of the pancreas. Incretins are an example of such molecules. Incretins potentiate glucose-induced insulin secretion from the pancreas, Incretins such as glucagon-like peptide-1 (7–36) amide ("GLP-1"; or the lizard analog Exendin-4) and gastric inhibitory polypeptide ("GIP") have been demonstrated to be insulinotropic, i.e., their presence or stabilization can maintain acute glycaemic control by their insulin-secretive effects (42, 18). GIP and GLP-1 are responsible for over 50% of nutrient-stimulated insulin secretion. Upon release into the circulation, GIP and GLP-1 are rapidly inactivated by the circulating enzyme dipeptidyl peptidase IV (DP IV). GIP and GLP-1 make up the endocrine component of the entero-insular (gut-pancreas) axis—a concept describing the neural, endocrine and substrate signaling pathways between the small intestine and the islets of Langerhans (9). Together, the incretins are responsible for over 50% of nutrient-stimulated insulin release, In addition, the incretins share a number of non-insulin mediated effects that contribute towards effective glucose homeostasis. GIP and GLP-1 have both been shown to inhibit gastric motility and secretion (10, 11), to promote β-cell glucose competence (12), and to stimulate insulin gene transcription and biosynthesis (13, 14). In addition, GIP has been reported to play a role in the regulation of fat metabolism (15) while GLP-1 has been shown to stimulate β-cell differentiation and growth (16), as well as to restore islet-cell glucose responsiveness (17). Additionally, it has been demonstrated that GLP-1 acts as an islet growth hormone by stimulating β-cell proliferation, cell mass increase and by promoting undifferentiated pancreatic cells to become specialized cells of the islet of Langerhans. Such cells show improved secretion of insulin and glucagon (43,44).

It has been previously proposed to apply exogenous bioactive GLP-1, or its analogs, to either stimulate islet cell regeneration in vivo, or to obtain pancreatic cells from diabetes mellitus patients and to treat such cells ex vivo in tissue culture using bioactive GLP-1. This ex vivo treatment was considered to facilitate regeneration and/or differentiation of islet cells which could then synthesis and secrete insulin or glucagon (45,46).

However, such a treatment regime requires the enteral or parenteral application of bioactive GLP-1 to patients, including the possibility of surgery. It is one aspect to obviate the need for surgical treatment, enteral or parenteral applications of bioactive GLP-1.

References

1. Kieffer T J, McIntosh C H, Pederson R A: Degradation of glucose-dependent insulinotropic polypeptide and truncated glucagon-like peptide 1 in vitro and in vivo by dipeptidyl peptidase IV. *Endocrinology* 136: 3585–3596, 1995
2. Mentlein R: Dipeptidyl-peptidase IV (CD26)—role in the inactivation of regulatory peptides. *Regul Pept* 85: 9–24, 1999
3. Pospisilik J A, Hinke S A, Pederson R A, Hoffmann T, Rosche F, Schlenzig D, Glund K, Heiser U, McIntosh C H, Demuth H: Metabolism of glucagon by dipeptidyl peptidase IV (CD26). *Regul Pept* 96: 133–141, 2001
4. Suzuki S, Kawai K, Ohashi S, Mukai H, Yamashita K: Comparison of the effects of various C-terminal and N-terminal fragment peptides of glucagon-like peptide-1 on insulin and glucagon release from the isolated perfused rat pancreas. *Endocrinology* 125: 3109–3114, 1989
5. Schmidt W, Siegel E, Ebert R, Creuzfeldt W: N-terminal tyrosine-alanine is required for the insulin releasing activity of glucose-dependent insulinotropic polypeptide (GIP). *Eur J Clin Invest* 16: A9, 1986
6. Pauly R P, Rosche F, Wermann M, McIntosh C H, Pederson R A, Demuth H U: Investigation of glucose-dependent insulinotropic polypeptide-(1–42) and glucagon-like peptide-1-(7–36) degradation in vitro by dipeptidyl peptidase IV using matrix-assisted laser desorption/ionization-time of flight mass spectrometry. A novel kinetic approach. *J Biol Chem* 271: 23222–23229, 1996
7. Deacon C F, Nauck M A, Meier J, Hucking K, Holst J J: Degradation of endogenous and exogenous gastric inhibitory polypeptide in healthy and in type 2 diabetic subjects as revealed using a new assay for the intact peptide. *J Clin Endocrinol Metab* 85: 3575–3581, 2000
8. Hansen L, Deacon C F, Orskov C, Holst J J: Glucagon-like peptide-1-(7–36)amide is transformed to glucagon-like peptide-1-(9–36)amide by dipeptidyl peptidase IV in the capillaries supplying the L cells of the porcine intestine. *Endocrinology* 140: 5356–5363, 1999
9. Unger R H, Eisentraut A M: Entero-insular axis. *Arch Intern Med* 123: 261–266, 1969
10. Schirra J, Katschinski M, Weidmann C, Schafer T, Wank U, Arnold R, Goke B: Gastric emptying and release of incretin hormones after glucose ingestion in humans. *J Clin Invest* 97: 92–103, 1996
11. Pederson R A, Brown J C: Inhibition of histamine-, pentagastrin-, and insulin-stimulated canine gastric secretion by pure "gastric inhibitory polypeptide". *Gastroenterology* 62: 393–400, 1972
12. Huypens P, Ling Z, Pipeleers D, Schuit F: Glucagon receptors on human islet cells contribute to glucose competence of insulin release. *Diabetologia* 43: 1012–1009, 2000
13. Fehmann H-C, Habener J F: Insulinotropic hormone glucagon-like peptide-1 (7–37) stimulation of proinsulin gene expression and proinsulin biosynthesis in insulinoma beta TC-1 cells. *Endocrinology* 130: 159–16., 1992
14. Drucker D J, Philippe J, Mojsov S, Chick W L, Habener J F: Glucagon-like peptide I stimulates insulin gene expression and increases cyclic AMP levels in a rat islet cell line. *Proc Natl Acad Sci USA* 84: 3434–3438, 1987
15. Pederson R: Gastric Inhibitory Polypeptide. In: Gut Peptides (J H Walsh, G J Dockray, eds.), pp. 217–259, Raven Press, Ltd, New York, 1994

16. Hui H, Wright C, Perfetti R., Glucagon-like peptide 1 induces differentiation of islet duodenal homeobox-1-positive pancreatic ductal cells into insulin-secreting cells. *Diabetes* 50: 785–796, 2001
17. Zawalich W S, Zawalich K C, Rasmussen H: Influence of glucagon-like peptide-1 on beta cell responsiveness. *Regul Pept* 44: 277–283, 1993
18. Pauly R, Demuth H-U, Rosche F, Schmidt J, White H, McIntosh C, Pederson R: Inhibition of dipeptidyl peptidase IV (DP IV) in rat results in improved glucose tolerance (Abstract). *Regul Pept* 64: 148, 1996
19. Pederson R A, White H A, Schlenzig D, Pauly R P, McIntosh C H, Demuth H U: Improved glucose tolerance in Zucker fatty rats by oral administration of the dipeptidyl peptidase IV inhibitor isoleucine thiazolidide. *Diabetes* 47: 1253–1258, 1998
20. Balkan B, Kwasnik L, Miserendino R, Holst J J, Li X: Inhibition of dipeptidyl peptidase IV with NVP-DPP728 increases plasma GLP-1 (7–36 amide) concentrations and improves oral glucose tolerance in obese Zucker rats. *Diabetologia* 42: 1324–1331, 1999
21. Lynn F C, Pamir N, Ng E H, McIntosh C H, Kieffer T J, Pederson R A: Defective glucose-dependent insulinotropic polypeptide receptor expression in diabetic fatty Zucker rats. *Diabetes* 50: 1004–1011, 2001
22. Demuth H U: Recent developments in inhibiting cysteine and serine proteases. *J Enzyme Inhib* 3: 249–78, 1990
23. Jia X, Elliott R, Kwok Y N, Pederson R A, McIntosh C H: Altered glucose dependence of glucagon-like peptide 1(7–36)-induced insulin secretion from the Zucker (fa/fa) rat pancreas. *Diabetes* 44: 495–500, 1995
24. Matsuda M, DeFronzo R A: Insulin sensitivity indices obtained from oral glucose tolerance testing: comparison with the euglycaemic insulin clamp. *Diabetes Care* 22: 1462–70, 1999
25. Brownsey R W, Denton R M: Evidence that insulin activates fat-cell acetyl-CoA carboxylase by increased phosphorylation at a specific site. *Biochem J* 202: 77–86, 1982
26. Thomas J A, Schlender K K, Larner J: A rapid filter paper assay for UDPglucose-glycogen glucosyltransferase, including an improved biosynthesis of UDP-14C-glucose. *Anal Biochem* 25: 486–499, 1968
27. Pederson R A, Buchan A M, Zahedi-Asl S, Chan C B, Brown J C: Effect of jejunoileal bypass in the rat on the enteroinsular axis. *Regul Pept* 5: 53–63, 1982
28. Finegood D T, McArthur M D, Kojwang D, Thomas M J, Topp B G, Leonard T, Buckingham R E: Beta-cell mass dynamics in Zucker diabetic fatty rats. Rosiglitazone prevents the rise in net cell death. *Diabetes* 50: 1021–1029, 2001
29. Ahren B, Holst J J, Martensson H, Balkan B: Improved glucose tolerance and insulin secretion by inhibition of dipeptidyl peptidase IV in mice. *Eur J Pharmacol* 404: 239–245, 2000
30. Wang Y, Montrose-Rafizadeh C, Adams L, Raygada M, Nadiv O, Egan J M: GIP regulates glucose transporters, hexokinases, and glucose-induced insulin secretion in RIN 1046-38 cells. *Mol Cell Endocrinol* 116: 81–87, 1996
31. Wang Y, Egan J M, Raygada M, Nadiv O, Roth J, Montrose-Rafizadeh C: Glucagon-like peptide-1 affects gene transcription and messenger ribonucleic acid stability of components of the insulin secretory system in RIN 1046-38 cells. *Endocrinology* 136: 4910–4917, 1995
32. Demuth H-U, Hoffmann T, Glund K, McIntosh C H S, Pederson R A, Fuecker K, Fischer S, Hanefeld M: Single dose treatment of diabetic patients by the inhibitor P32/98 (Abstract). *Diabetes* 49 (Suppl. 1): 413-P, 2000
33. Glund K, Hoffmann T, Demuth H-U, Banke-Bochita J, Rost K L, Fuder H: Single dose-escalation study to investigate the safety and tolerability of the DP IV-inhibitor P32/98 in healthy volunteers (Abstract). *Exp Clin Endocrinol Diabetes* 108:159, 2000
34. Yang H, Egan J M, Wang Y, Moyes C D, Roth J, Montrose M H, Montrose-Rafizadeh C: GLP-1 action in L6 myotubes is via a receptor different from the pancreatic GLP-1 receptor. *Am J Physiol* 275: C675–C683, 1998
35. O'Harte F P, Abdel-Wahab Y H, Conlon J M, Flatt P R: Amino terminal glycation of gastric inhibitory polypeptide enhances its insulinotropic action on clonal pancreatic B-cells. *Biochim Biophys Acta* 1425: 319–327, 1998
36. Mizuno A, Kuwajima M, Ishida K, Noma Y, Murakami T, Tateishi K, Sato I, Shima K: Extrapancreatic action of truncated glucagon-like peptide-I in Otsuka Long-Evans Tokushima Fatty rats, an animal model for non-insulin-dependent diabetes mellitus. *Metabolism* 46: 745–749, 1997
37. Alcantara A I, Morales M, Delgado E, Lopez-Delgado M I, Clemente F, Luque M A, Malaisse W J, Valverde I, Villanueva-Penacarrillo M L: Exendin-4 agonist and exendin(9–39)amide antagonist of the GLP-1(7–36) amide effects in liver and muscle. *Arch Biochem Biophys* 341: 1–7, 1997
38. Young A A, Gedulin B R, Bhavsar S, Bodkin N, Jodka C, Hansen B, Denaro M: Glucose-lowering and insulin-sensitizing actions of exendin-4. Studies in obese diabetic (ob/ob, db/db) Mice, diabetic fatty Zucker rats, and diabetic rhesus monkeys (Macaca mulatta). *Diabetes* 48: 1026–1034, 1999
39. Freyse E J, Becher T, El-Hag O, Knospe S, Göke B, Fischer U: Blood glucose lowering and glucagonostatic effects of glucagon-like peptide I in insulin-deprived diabetic dogs. *Diabetes* 46: 824–828, 1997
40. Larsen J, Jallad J, Damsbo P: One week continuous infusion of GLP-1 (7–37) improves glycaemic control in NIDDM (Abstract). *Diabetes* 45: 233A, 1996
41. Rachman J, Barrow B, Levy J, Turner R: Near normalisation of diurnal glucose concentrations by continuous administrations of glucagon-like peptide-1 (GLP-1) in subjects with NIDDM. *Diabetologia* 40: 205–211, 1997
42. Demuth, H. U. et al., DE 196 16 486:1–6, 1996
43. Yaekura, K. et al., IN: VIP, PACAP, and Related Peptides, W. G. Forssmann and S. I. Said (eds.), New York: New York Academy of Sciences, 1998, p. 445–450
44. Buteau, J. et al., Diabetologia 42(7): 856–864, 1999
45. Zhou, J. et al., *Diabetes,* 48(12):2358–2366, 1999
46. Xu, G. et al., *Diabetes,* 48(12):2270–2276, 1999
47. Sato, A. et al., *Pancreas* 2002, 25 (1), 86–93
48. Filipsson, K. et al.: Neuropeptide Pituitary Adenylate Cyclase—Activating Polypeptide and Islet Function, *Diabetes,* 50 (9):1959–1969, 2001
49. Sedo & Malik, Dipeptidyl peptidase IV-like molecules: homologous proteins or homologous activities, Biochimica et Biophysica Acta 2001, 36506: 1–10

SUMMARY

The present invention relates to a novel method in which the reduction of activity in the enzyme Dipeptidyl Peptidase (DP IV or CD 26) or of DP IV-like enzyme activity in the blood of mammals induced by effectors of the enzyme leads as a causal consequence to a reduced degradation of the gastrointestinal polypeptide Glucagon-like peptide amide-$1_{7-36}$ (GLP-$1_{7-36}$) (or structurally related functional analogs of this peptide, such as GLP-1$_{7-37}$, or truncated but biologically active fragments of GLP-1$_{7-36}$) by DP IV and DP IV-like enzymes. Such treatment will result in a reduction or delay in the decrease of the concentration of functionally active GLP-1 (including GLP-1-derived) circulating peptide hormones or of their analogs. The phrase DP IV-like enzymes is intended to include those enzymes which may be related to DP IV and have similar dipeptide cleavage enzyme activity as DP IV but which none-the-less may be distinguishable from DP IV. In particular, DP IV-like enzymes are structurally related enzymes to DP IV which may share a certain sequence homology to the DP IV sequence, but which share even if they are not structurally related (by convergent evolution) the substrate specificity of DP IV of removing dipeptides from the N-termini of polypeptides by cleaving after a penultimate proline residue. Such enzymes—including DP IV, DP II at one hand and attractin on the other hand—are also capable to remove dipeptides with a penultimate alanine (or serine or glycine residues) from the N-termini of polypeptides but usually with reduced catalytic efficacy as compared to the post-proline cleavage (Yaron & Naider, 1993). They show the common feature that they accommodate in the Pro-position of the target-protein also Ala, Ser, Thr and other amino acids with small hydrophobic side-chains as, Gly or Val. The hydrolytic efficacy is ranked Pro>Ala>>Ser, Thr>>Gly, Val. While the proteins DP IV, DP II, FAPα (Seprase), DP 6, DP 8 and DP 9 are structurally related and show a high sequence homology, attractin is an extraordinary functional DP IV-like enzyme (49).

Further DP IV-like enzymes are disclosed in WO 01/19866, WO 02/04610, WO 02/34900 and WO02/31134. WO 01/19866 discloses human dipeptidyl aminopeptidase 8 (DPP8) with structural und functional similarities to DP IV and fibroblast activation protein (FAP). The dipeptidyl peptidase IV-like enzyme of WO 02/04610 is well known in the art. In the GENE BANK data base, this enzyme is registered as KIAA1492 (registration in February 2001, submitted on Apr. 4, 2000, AB040925) and in the MEROPS data base. WO 02/34900 discloses a dipeptidyl peptidase 9 (DPP9) with significant homology to the amino acid sequences of DP IV and DPP8. WO 02/31134 discloses three DP IV-like enzymes, DPRP1, DPRP2 and DPRP3. Sequence analysis revealed that DPRP1 is identical to DPP8, as disclosed in WO 01/19866, that DPRP2 is identical to DPP9 and that DPRP3 is identical to KIAA1492 as disclosed in WO 02/04610.

As a consequence of the resulting enhanced stability of the endogenous GLP-1 (including GLP-1-derived) circulating peptides caused by the inhibition of DP IV-activity, GLP-1 activity is prolonged resulting in functionally active GLP-1 (including GLP-1-derived) circulating peptide hormones facilitating growth-hormone-like stimulation of pancreatic cells in such a way that these cells proliferate to functionally active cells of the Islets of Langerhans. Additionally, insensitive pancreatic cells or impaired pancreatic cells may be transformed into functionally active cells of the islets of Langerhans when exposed to GLP-1.

It was expected, that the transformation of insensitive pancreatic cells or impaired pancreatic cells to functionally active cells of the islets of Langerhans results in an increased insulin secretion and in an increased insulin level in blood plasma. Surprisingly, in studies in healthy human volunteers and obese, diabetic Zucker rats, the insulin level decreased after treatment with the DP IV-inhibitor isoleucyl thiazolidine hemifumarate (P32/98) (see examples 1 and 2, respectively). Nevertheless, the resulting regeneration of the islets of Langerhans does change the efficacy of endogenous insulin and other islet hormones, such as glucagon, in such a way that stimulation of carbohydrate metabolism of a treated mammal is effected. As a result, the blood glucose level drops below the glucose concentration characteristic for hyperglycemia, as shown in examples 1 and 2. The mechanism triggering these effects is not known in detail. However, this resulting regeneration of the islet cells further affects anomalies of the metabolism including glucosuria, hyperlipidaemia as well as severe metabolic acidosis and Diabetes mellitus, by preventing or alleviating these sequelae. It has been further surprisingly discovered that the chronic oral administration of effectors of DP IV, such as orally active inhibitors thereof, can also result in increased rate of progression to satiety during nutrient ingestion, decreased weight, decreases in chronic or long-term weight gains, and improved insulin sensitivity in muscles. Still another unforeseen effect involves the increased availability of hormones which are not regulated primarily in the short term by nutrient ingestion (e.g. acute changes in glucose levels) and which can improve β-cell activity and/or increasing differentiation of pancreatic cells to β-cells resulting in measurably improved insulin output.

In contrast to other proposed methods known in the art, such as pancreatic cell or tissue transplantation or ex-vivo treatment of pancreatic cells using GLP-1 or exendin-4 followed by re-implantation of the treated cells, the present invention does not cause or require complicated and costly surgery, and provides an orally available therapy. The instant invention represents a novel approach for lowering the elevated concentration of blood glucose, modifying satiety, weight gain, muscle sensitivity amongst other related effects. It is commercially useful and suitable for use in a therapeutic regime, especially concerning human disease, many of which are caused by prolonged elevated or blood glucose levels or improper or inadequate β-cell activity.

BRIEF DESCRIPTION OF THE FIGURES

Further understanding of the instant invention may be had by reference to the figures wherein:

FIG. 6 shows body weight and water intake measured in DP IV-inhibitor treated (open circles) or control (solid squares; n=6) VDF rats. Body weight (A), and water intake (B) were measured along with morning and evening blood glucose levels and food intake (not shown) every two days. Statistical significance (p<0.05) is indicated by an asterisk;

FIG. 11 shows adipose tissue glycogen synthase activity (A) and uptake of 3-O-[$^{14}$C] methyl-D-glucose into soleus muscle strips (B) isolated from VDF rats after twelve weeks of P32/98 treatment (open bars) or a control 1% cellulose solution (solid bars) (n=6). An asterisk represents a statistically significant difference relative to the corresponding control value (* p<0.05, ** p<0.01), while "a" represents a statistically significant difference from basal ([Insulin]=0 µU/ml);

DETAILED DESCRIPTION

Figure 1:
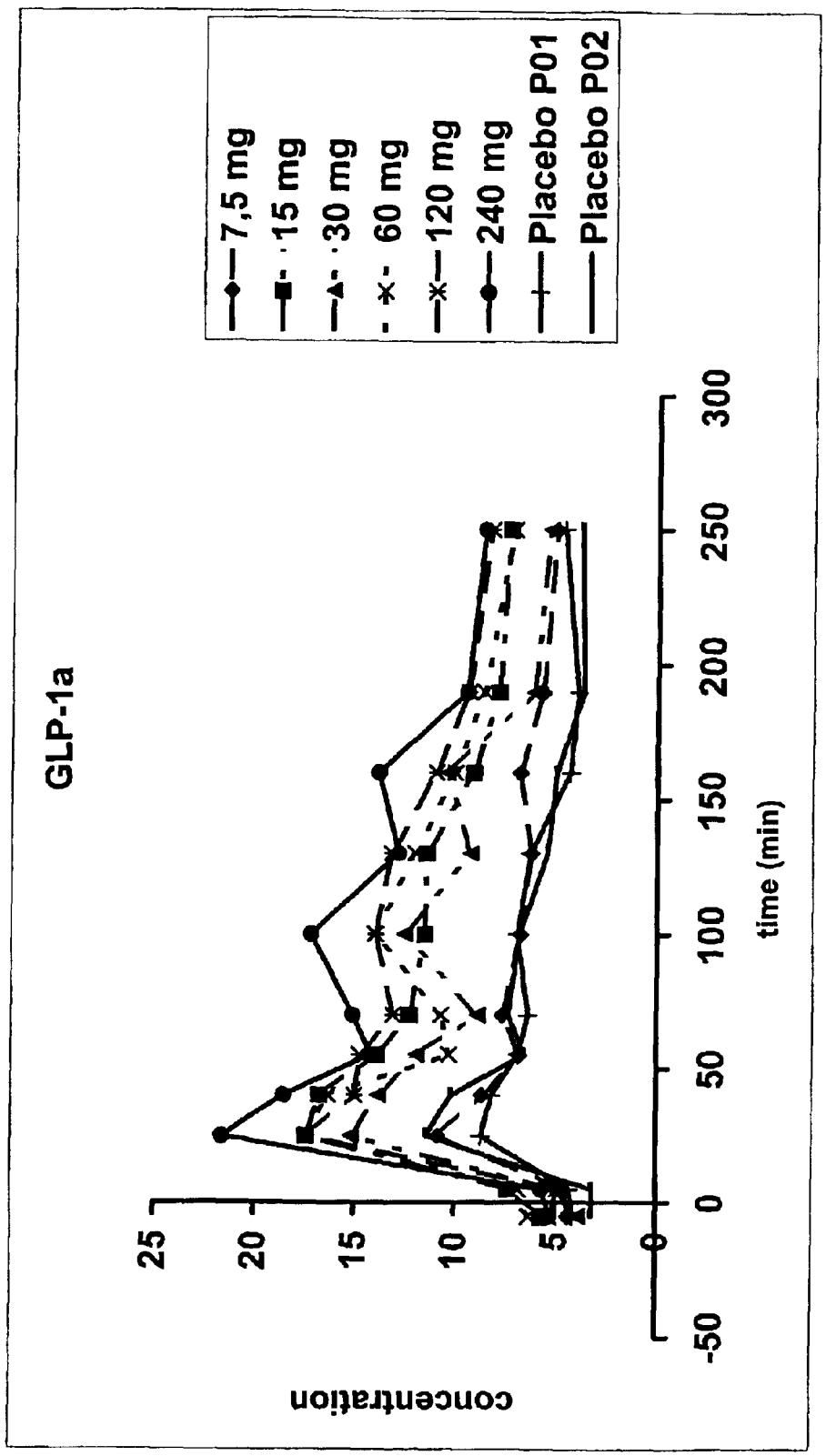
FIG. 1 is a graphical representation of the time-dependency of circulating bioactive GLP-1 in humans (n=36) depending on the orally applied DP IV-inhibitor formulation P32/98.

The present invention pertains to a novel method for differentiating and/or reconstituting pancreatic cells. The resulting regeneration of the islet cells of Langerhans will positively affect the synthesis and release of endogenous insulin and other islet hormones, such as glucagon, in such a manner that the stimulation of carbohydrate metabolism will be effected.

Glucose-induced insulin secretion is modulated by a number of hormones and neurotransmitters. Of specific interest are the two gut hormones, glucagon-like peptide-1 (GLP-1) and gastric inhibitory peptide (GIP), both of which are insulinotropic agents. Insulinotropic agents can stimulate, or cause the stimulation of, the synthesis or expression of the hormone insulin.

GLP-1 is a potent intestinal insulinotropic agent that augments insulin secretion and acutely lowers glucose levels, including levels observed in Type I and Type II diabetes. GLP-1 is formed by alternative tissue-specific cleavages in the L cells of the intestine, the α-cells of the endocrine pancrease, and neurons in the brain. GIP is synthesized and released from the duodenum and proximal jejunum postprandially. Its release depends upon several factors including meal content and pre-existing health status. It was initially discovered and named for its gastric acid inhibitory properties. However, as research into this hormone has progressed, more relevant physiological roles have been elucidated. Specifically, GIP is an insulinotropic agent with a stimulatory effect on insulin synthesis and release.

DP IV is an enzyme that is an exopeptidase which selectively cleaves peptides after penultimate N-terminal proline and alanine residues. Endogenous substrates for this enzyme include the incretins, such as glucose-dependent insulinotropic polypeptides, like GIP and GLP-1. In the presence of DP IV, these hormones are enzymatically reduced to inactive forms. The inactive form of GIP and GLP cannot induce insulin secretion, thus blood glucose levels are elevated, especially in the hyperglycaemic state. Elevated blood glucose levels have been associated with many different pathologies, including diabetes mellitus (Type 1 and 2) and the sequelae accompanying diabetes mellitus.

It has also been discovered that DP IV plays a role in T-cell-mediated immune responses, for example, in transplantations. Inhibition of DP IV has been demonstrated to prolong cardiac allografts. Additionally, the inhibition of DP IV has contributed to the suppression of rheumatoid arthritis. DP IV has also been attributed a role in HIV's penetration into T-cells (T-helper cells).

Agents such as N-(N'-substituted glycyl)-2-cyanopyrrolidines, L-threo-isoleucyl thiazolidine (P32/98), L-allo-isoleucyl thiazolidine, L-threo-isoleucyl pyrrolidine, and L-allo-isoleucyl pyrrolidine have been developed which inhibit the enzymatic activity of DP IV are described in U.S. Pat. No. 6,001,155, WO 99/61431, WO 99/67278, WO 99/67279, DE 198 34 591, WO 97/40832, DE 196 16 486 C 2, WO 98/19998, WO 00/07617, WO 99/38501, and WO 99/46272. Further examples of low molecular weight dipeptidyl peptidase IV inhibitors are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, amino-acyl-borono-prolyl-inhibitors and cyclopropyl-fused pyrrolidines. Inhibitors of dipeptidyl peptidase IV are described in U.S. Pat. Nos. 6,011,155; 6,107,317; 6,110,949; 6,124,305; 6,172,081; WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, the teachings of which are herein incorporated by reference in their entirety concerning these inhibitors, their uses, definition and their production. The goal of these agents is to inhibit DP IV, and by doing so, to lower blood glucose levels thereby effectively treating hyperglycemia and attendant diseases associated with elevated levels of glucose in the blood. The inventors hereof have surprisingly discovered that such agents can be advantageously employed for an entirely different therapeutic purpose, then previously known by those skilled in the art.

In one illustrative embodiment, the present invention relates to the use of dipeptide-like compounds and compounds analogous to dipeptide compounds that are formed from an amino acid and a thiazolidine or pyrrolidine group, and salts thereof, referred to hereinafter as dipeptide-like compounds. Preferably the amino acid and the thiazolidine or pyrrolidine group are bonded with an amide bond.

Especially suitable for that purpose according to the invention are dipeptide compounds in which the amino acid is preferably selected from a natural amino acid, such as, for example, leucine, valine, glutamine, glutamic acid, proline, isoleucine, asparagines and aspartic acid.

The dipeptide-like compounds used according to the invention exhibit at a concentration (of dipeptide compounds) of 10 $\mu$M, a reduction in the activity of plasma dipeptidyl peptidase IV or DP IV-analogous enzyme activities of at least 10%, especially of at least 40%. Frequently a reduction in activity of at least 60% or at least 70% is also required. Preferred effectors may also exhibit a reduction in activity of a maximum of 20% or 30%.

Preferred compounds are N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl pyrrolidine and glutaminyl thiazolidine of formulas 1 and 2:

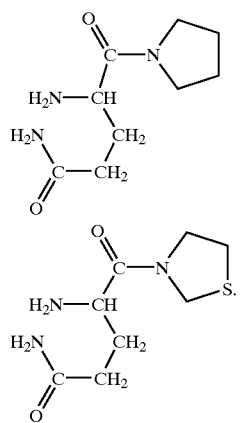

Further preferred compounds are given in Table 1.
The salts of the dipeptide-like compounds can be present in a molar ratio of dipeptide (-analogous) component to salt component of 1:1 or 2:1. Such a salt is, for example, (Ile-Thia)$_2$ fumaric acid.

TABLE 1

Structures of further preferred dipeptide compounds

Effector

H-Asn-pyrrolidine
H-Asn-thiazolidine
H-Asp-pyrrolidine
H-Asp-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine
H-Glu(NHOH)-thiazolidine
H-His-pyrrolidine
H-His-thiazolidine
H-Pro-pyrrolidine
H-Pro-thiazolidine
H-Ile-azididine
H-Ile-pyrrolidine
H-L-allo-Ile-thiazolidine
H-Val-pyrrolidine
H-Val-thiazolidine In another preferred embodiment, the present invention provides the use of substrate-like peptide compounds of formula 3 useful for competitive modulation of dipeptidyl peptidase IV catalysis:

(3)

wherein
A, B, C, D and E are independently any amino acid moieties including proteinogenic amino acids, non-proteinogenic amino acids, L-amino acids and D-amino acids and wherein E and/or D may be absent.
Further conditions regarding formula (3):
A is an amino acid except a D-amino acid,
B is an amino acid selected from Pro, Ala, Ser, Gly, Hyp, acetidine-(2)-carboxylic acid and pipecolic acid,
C is any amino acid except Pro, Hyp, acetidine-(2)-carboxylic acid, pipecolic acid and except N-alkylated amino acids, e.g. N-methyl valine and sarcosine,
D is any amino acid or missing, and
E is any amino acid or missing,
or:
C is any amino acid except Pro, Hyp, acetidine-(2)-carboxylic acid, pipecolic acid, except N-alkylated amino acids, e.g. N-methyl valine and sarcosine, and except a D-amino-acid;
D is any amino acid selected from Pro, Ala, Ser, Gly, Hyp, acetidine-(2)-carboxylic acid and pipecolic acid, and
E is any amino acid except Pro, Hyp, acetidine-(2)-carboxylic acid, pipecolic acid and except N-alkylated amino acids, e.g. N-methyl valine and sarcosine.
Examples of amino acids which can be used in the present invention are L and D-amino acids, N-methyl-amino-acids; allo- and threo-forms of Ile and Thr, which can, e.g. be $\alpha$-, $\beta$- or $\omega$-amino acids, whereof $\alpha$-amino acids are preferred.
Examples of amino acids throughout the claims and the description are: aspartic acid (Asp), glutamic acid (Glu), arginine (Arg), lysine (Lys), histidine (His), glycine (Gly), serine (Ser) and cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-amino octanoic acid (Aoa), azetidine-(2)-carboxylic acid (Ace), pipecolic acid (Pip), 3-amino propionic, 4-amino butyric and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), Acetyl-Lys, modified amino acids such as phosphoryl-serine (Ser(P)), benzyl-serine (Ser (Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cis Hyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-Amino-4-cyanobutyric acid (Cba), cycloalkane-carboxylic aicds.

Examples of ω-amino acids are e.g.: 5-Ara (aminoraleric acid), 6-Ahx (aminohexanoic acid), 8-Aoc (aminooctanoic aicd), 9-Anc (aminovanoic aicd), 10-Adc (aminodecanoic acid), 11-Aun (aminoundecanoic acid), 12-Ado (aminododecanoic acid).

Further amino acids are: indanylglycine (Ig1), indoline-2-carboxylic acid (Idc), octahydroindole-2-carboxylic acid (Oic), diaminopropionic acid (Dpr), diaminobutyric acid (Dbu), naphtylalanine (1-Nal), (2-Nal), 4-aminophenylalanin (Phe(4-NH$_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe (3,4-Cl$_2$)), 3-fluorophenylalanine (Phe(3-F)), 4-fluorophenylalanine (Phe(4-F)), 3,4-fluorophenylalanine (Phe(3,4-F$_2$)), pentafluorophenylalanine (Phe(F$_5$)), 4-guanidinophenylalanine (Phe(4-guanidino)), homophenylalanine (hPhe), 3-jodophenylalanine (Phe(3-J)), 4 jodophenylalanine (Phe(4-J)), 4-methylphenylalanine (Phe(4-Me)), 4-nitrophenylalanine (Phe-4-NO$_2$)), biphenylalanine (Bip), 4-phosphonomehtylphenylalanine (Pmp), cyclohexyglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-J$_2$)), d-methyl-tyrosine (Tyr(Me)), 3-NO$_2$-tyrosine (Tyr(3-NO$_2$)), phosphotyrosine (Tyr(PO$_3$H$_2$)), alkylglycine, 1-aminoindane-1-carboxy acid, 2-aminoindane-2-carboxy acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly(NH$_2$)), diaminobutyric acid (Dab), 1,3-dihydro-2H-isoinole-carboxylic acid (Disc), homocylcohexylalanin (hCha), homophenylalanin (hPhe oder Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienryl)-alanine (Tha)

Other amino acid substitutions for those encoded in the genetic code can also be included in peptide compounds within the scope of the invention and can be classified within this general scheme.

Proteinogenic amino acids are defined as natural protein-derived α-amino acids. Non-proteinogenic amino acids are defined as all other amino acids, which are not building blocks of common natural proteins.

The resulting peptides may be synthesized as the free C-terminal acid or as the C-terminal amide form. The free acid peptides or the amides may be varied by side chain modifications. Such side chain modifications include for instance, but not restricted to, homoserine formation, pyroglutamic acid formation, disulphide bond formation, deamidation of asparagine or glutamine residues, methylation, t-butylation, t-butyloxycarbonylation, 4-methylbenzylation, thioanysilation, thiocresylation, benzyloxymethylation, 4-nitrophenylation, benzyloxycarbonylation, 2-nitrobencoylation, 2-nitrosulphenylation, 4-toluenesulphonylation, pentafluorophenylation, diphenylmethylation, 2-chlorobenzyloxycarbonylation, 2,4,5-trichlorophenylation, 2-bromobenzyloxycarbonylation, 9-fluorenylmethyloxycarbonylation, triphenylmethylation, 2,2,5,7,8,-pentamethylchroman-6-sulphonylation, hydroxylation, oxidation of methionine, formylation, acetylation, anisylation, benzylation, bencoylation, trifluoroacetylation, carboxylation of aspartic acid or glutamic acid, phosphorylation, sulphation, cysteinylation, glycolysation with pentoses, deoxyhexoses, hexosamines, hexoses or N-acetylhexosamines, farnesylation, myristolysation, biotinylation, palmitoylation, stearoylation, geranylgeranylation, glutathionylation, 5'-adenosylation, ADP-ribosylation, modification with N-glycolylneuraminic acid, N-acetylneuraminic acid, pyridoxal phosphate, lipoic acid, 4'-phosphopantetheine, or N-hydroxysuccinimide.

In the compounds of formula (3), the amino acid moieties A, B, C, D, and E are respectively attached to the adjacent moiety by amide bonds in a usual manner according to standard nomenclature so that the amino-terminus (N-terminus) of the amino acids (peptide) is drawn on the left and the carboxyl-terminus of the amino acids (peptide) is drawn on the right. (C-terminus)

Until the present invention by Applicants, known peptide substrates of the proline-specific serine protease dipeptidyl peptidase IV in vitro are the tripeptides Diprotin A (Ile-Pro-Ile), Diprotin B (Val-Pro-Leu) and Diprotin C (Val-Pro-Ile). Applicants have unexpectedly discovered that the compounds disclosed herein above and below act as substrates of dipeptidyl peptidase IV in vivo in a mammal and, in pharmacological doses, improve insulin sensitivity and islet signaling and alleviate pathological abnormalities of the metabolism of mammals such as glucosuria, hyperlipidaemia, metabolic acidosis and diabetes mellitus by competitive catalysis.

Preferred peptide compounds are listed in table 2.

TABLE 2

Examples of peptide substrates

| Peptide | Mass (calc.) | Mass (exp.)[1] [M + H$^+$] |
|---|---|---|
| 2-Amino octanoic acid-Pro-Ile | 369.5 | 370.2 |
| Abu-Pro-Ile | 313.4 | 314.0 |
| Aib-Pro-Ile | 313.4 | 314.0 |
| Aze-Pro-Ile | 311.4 | 312.4 |
| Cha-Pro-Ile | 381.52 | 382.0 |
| Ile-Hyp-Ile | 356.45 | 358.2 |
| Ile-Pro-allo-Ile | 341.4 | 342.0 |

TABLE 2-continued

Examples of peptide substrates

| Peptide | Mass (calc.) | Mass (exp.)[1] [M + H+] |
|---|---|---|
| Ile-Pro-t-butyl-Gly | 341.47 | 342.36 |
| Ile-Pro-Val | 327.43 | 328.5 |
| Nle-Pro-Ile | 341.45 | 342.2 |
| Nva-Pro-Ile | 327.43 | 328.2 |
| Orn-Pro-Ile | 342.42 | 343.1 |
| Phe-Pro-Ile | 375.47 | 376.2 |
| Phg-Pro-Ile | 361.44 | 362.2 |
| Pip-Pro-Ile | 338.56 | 340.0 |
| Ser(Bzl)-Pro-Ile | 405.49 | 406.0 |
| Ser(P)-Pro-Ile | 395.37 | 396.0 |
| Ser-Pro-Ile | 315.37 | 316.3 |
| t-butyl-Gly-Pro-D-Val | 327.4 | 328.6 |
| t-butyl-Gly-Pro-Gly | 285.4 | 286.3 |
| t-butyl-Gly-Pro-Ile | 341.47 | 342.1 |
| t-butyl-Gly-Pro-Ile-amide | 340.47 | 341.3 |
| t-butyl-Gly-Pro-t-butyl-Gly | 341.24 | 342.5 |
| t-butyl-Gly-Pro-Val | 327.4 | 328.4 |
| Thr-Pro-Ile | 329.4 | 330.0 |
| Tic-Pro-Ile | 387.46 | 388.0 |
| Trp-Pro-Ile | 414.51 | 415.2 |
| Tyr(P)-Pro-Ile | 471.47 | 472.3 |
| Tyr-Pro-allo-Ile | 391.5 | 392.0 |
| Val-Pro-allo-Ile | 327.4 | 328.5 |
| Val-Pro-t-butyl-Gly | 327.4 | 328.15 |
| Val-Pro-Val | 313.4 | 314.0 |

[1][M + H+] were determined by Electrospray mass spectrometry in positive ionization mode.

t-butyl-Gly is defined as:

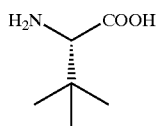

Ser(Bzl) and Ser(P) are defined as benzyl-serine and phosphoryl-serine, respectively. Tyr(P) is defined as phosphoryl-tyrosine.

Further preferred compounds are peptidylketones of formula 4:

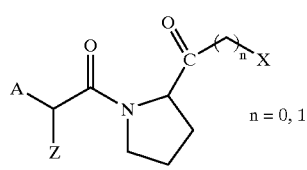

(4)

n = 0, 1 and pharmaceutically acceptable salts thereof, wherein:
A is selected from the following structures:

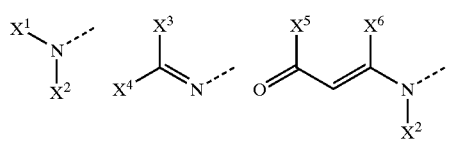

$X^1$ is H or an acyl or oxycarbonyl group including all amino acids and peptide residues, $X^2$ is H, —(CH)$_n$—NH—C$_5$H$_3$N—Y with n=2–4 or C$_5$H$_3$N—Y (a divalent pyridy residue) and Y is selected from H, Br, Cl, I, NO$_2$ or CN, $X^3$ is H or selected from an alkyl, alkoxy, halogen, nitro, cyano or carboxy substituted phenyl or pyridyl residue, $X^4$ is H or selected from an alkyl, alkoxy, halogen, nitro, cyano or carboxy substituted phenyl or pyridyl residue, $X^5$ is H or an alkyl, alkoxy or phenyl residue, $X^6$ is H or an alkyl residue, for n=1
X is selected from: H, OR$^2$, SR$^2$, NR$^2$R$^3$, N$^+$R$^2$R$^3$R$^4$, wherein:

$R^2$ stands for acyl residues, which are substituted with alkyl, cycloalkyl, aryl or heteroaryl residues, or for all amino acids and peptidic residues, or alkyl residues, which are substituted with alkyl, cycloalkyl, aryl and by heteroaryl residues, $R^3$ stands for alkyl and acyl functions, wherein $R^2$ and $R^3$ may be embedded in ring structures of a saturated or unsaturated carbocyclic or heterocyclic structures, $R^4$ stands for alkyl residues, wherein $R^2$ and $R^4$ or $R^3$ and $R^4$ may be embedded in ring structures of a saturated or unsaturated carbocyclic or heterocyclic structures.

for n=0
X is selected from:

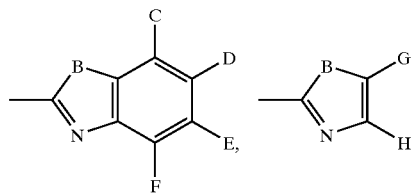

wherein

B stands for: O, S, NR$^5$, wherein R$^5$ is H, a alkyl or acyl, C, D, E, F, G, H are independently selected from alkyl and substituted alkyl residues, oxyalkyl, thioalkyl, aminoalkyl, carbonylalkyl, acyl, carbamoyl, aryl and heteroaryl residues; and Z is selected from H, or a branched or single chain alkyl residue from C$_1$–C$_9$ or a branched or single chain alkenyl residue from C$_2$–C$_9$, a cycloalkyl residue from C$_3$–C$_8$, a cycloalkenyl residue from C$_5$–C$_7$, a aryl- or heteroaryl residue, or a side chain selected from all side chains of all natural amino acids or derivatives thereof.

Preferably:
the acyl groups are C1–C6-acyl groups,
the alkyl groups are C1–C6-alkyl groups,
the alkoxy groups are C1–C6-alkoxy groups,
the aryl radicals are C5–C12 aryl radicals that have optionally fused rings,
the cycloalkyl radicals (carbocycles) are C3–C8-cycloalkyl radicals,
the heteroaryl radicals are C4–C11 aryl radicals that have optionally fused rings and, in at least one ring, from 1 to 4 hetero atoms, such as O, N and/or S,
peptide residues are corresponding residues consisting of from 2 to 50 amino acids,
the heterocyclic radicals are C2–C7-cycloalkyl radicals that have from 1 to 4 hetero atoms, such as O, N and/or S.

Further, according to the present invention compounds of formulas 5, 6, 7, 8, 9, 10 and 11, including all stereoisomers and pharmaceutical acceptable salts thereof can be used:

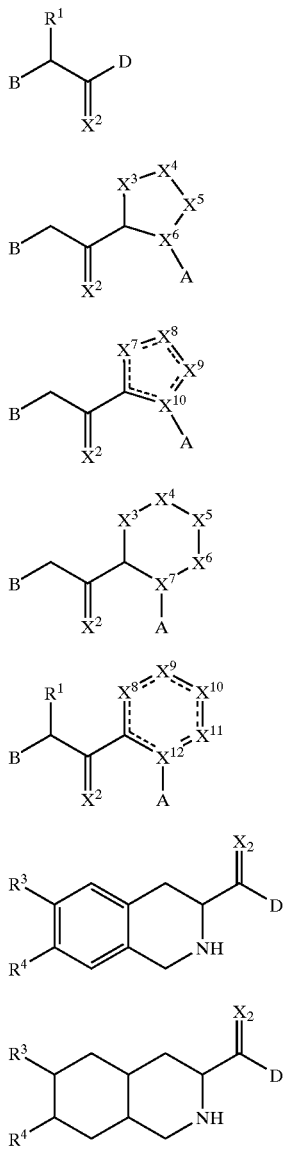

wherein:

R¹ is H, a branched or linear $C_1$–$C_9$ alkyl residue, a branched or linear $C_2$–$C_9$ alkenyl residue, a $C_3$–$C_8$ cycloalkyl-, $C_5$–$C_7$ cycloalkenyl-, aryl- or heteroaryl residue or a side chain of a natural amino acid or a derivative thereof, R³ and R⁴ are selected from H, hydroxy, alkyl, alkoxy, aryloxy, nitro, cyano or halogen, A is H or an isoster of a carbonic acid, like a functional group selected from CN, $SO_3H$, CONHOH, $PO_3R^5R^6$, tetrazole, amide, ester, anhydride, thiazole and imidazole, B is selected from:

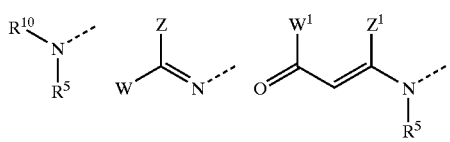

wherein

R⁵ is H, —$(CH)_n$—NH—$C_5H_3N$—Y with n=2–4 and $C_5H_3N$—Y (a divalent pyridyl residue) with Y=H, Br, Cl, I, $NO_2$ or CN, R¹⁰ is H, an acyl, oxycarbonyl or a amino acid residue, W is H or a phenyl or pyridyl residue, unsubstituted or substituted with one, two or more alkyl, alkoxy, halogen, nitro, cyano or carboxy residues, W¹ is H, an alkyl, alkoxy or phenyl residue, Z is H or a phenyl or pyridyl residue, unsubstituted or substituted with one, two or more alkyl, alkoxy, halogen, nitro, cyano or carboxy residues, Z¹ is H or an alkyl residue, D is a cyclic $C_4$–$C_7$ alkyl, $C_4$–$C_7$ alkenyl residue which can be unsubstituted or substituted with one, two or more alkyl groups or a cyclic 4–7-membered heteroalkyl or a cyclic 4–7-membered heteroalkenyl residue, X² is O, $NR^6$, $N^+(R^7)_2$, or S, X³ to X¹² are independently selected from $CH_2$, $CR^8R^9$, $NR^6$, $N^+(R^7)_2$, O, S, SO and $SO_2$, including all saturated and unsaturated structures, R⁶, R⁷, R⁸, R⁹ are independently selected from H, a branched or linear $C_1$–$C_9$ alkyl residue, a branched or linear $C_2$–$C_9$ alkenyl residue, a $C_3$–$C_8$ cycloalkyl residue, a $C_5$–$C_7$ cycloalkenyl residue, an aryl or heteroaryl residue, with the following provisos:

Formula 6: X⁶ is CH if A is not H,
Formula 7: X¹⁰ is C if A is not H,
Formula 8: X⁷ is CH if A is not H,
Formula 9: X¹² is C if A is not H.

Throughout the description and the claims the expression "acyl" can denote a $C_{1-20}$ acyl residue, preferably a $C_{1-8}$ acyl residue and especially preferred a $C_{1-4}$ acyl residue, "cycloalkyl" can denote a $C_{3-12}$ cycloalkyl residue, preferably a $C_4$, $C_5$ or $C_6$ cycloalkyl residue, "carbocyclic" can denote a $C_{3-12}$ carbocyclic residue, preferably a $C_4$, $C_5$ or $C_6$ carbocyclic residue. "Heteroaryl" is defined as an aryl residue, wherein 1 to 4, preferably 1, 2 or 3 ring atoms are replaced by heteroatoms like N, S or O. "Heterocyclic" is defined as a cycloalkyl residue, wherein 1, 2 or 3 ring atoms are replaced by heteroatoms like N, S or O. "Peptides" are selected from dipeptides to decapeptides, preferred are dipeptides, tripeptides, tetrapeptides and pentapeptides. The amino acids for the formation of the "peptides" can be selected from those listed above.

Because of the wide distribution of the protein in the body and the wide variety of mechanisms involving DP IV, DP IV-activity and DP IV-related proteins, systemic therapy (enteral or parenteral administration) with DP IV-inhibitors can result in a series of undesirable side-effects.

The problem to be solved was moreover, to provide compounds that can be used for targeted influencing of locally limited patho-physiological and physiological processes. The problem of the invention especially consists in obtaining locally limited inhibition of DP IV or DP IV-analogous activity for the purpose of targeted intervention in the regulation of the activity of locally active substrates, This problem is solved according to the invention by compounds of the general formula (12)

$$A—C \atop |\ \ \ \ \ \ \ \ \ \ \ \ \ \ (12) \atop B$$

wherein

A is an amino acid having at least one functional group in the side chain,

B is a chemical compound covalently bound to at least one functional group of the side chain of A, C is a thiazolidine, pyrrolidine, cyanopyrrolidine, hydroxyproline, dehydroproline or piperidine group amide-bonded to A.

In accordance with a preferred embodiment of the invention, pharmaceutical compositions are used comprising at least one compound of the general formula (12) and at least one customary adjuvant appropriate for the site of action.

Preferably A is an α-amino acid, especially a natural α-amino acid having one, two or more functional groups in the side chain, preferably threonine, tyrosine, serine, arginine, lysine, aspartic acid, glutamic acid or cysteine.

Preferably B is an oligopeptide having a chain length of up to 20 amino acids, a polyethylene glycol having a molar mass of up to 20 000 g/mol, an optionally substituted organic amine, amide, alcohol, acid or aromatic compound having from 8 to 50 C atoms.

Throughout the description and the claims the expression "alkyl" can denote a $C_{1-50}$ alkyl group, preferably a $C_{6-30}$ alkyl group, especially a $C_{8-12}$ alkyl group; for example, an alkyl group may be a methyl, ethyl, propyl, isopropyl or butyl group. The expression "alk", for example in the expression "alkoxy", and the expression "alkan", for example in the expression "alkanoyl", are defined as for "alkyl"; aromatic compounds are preferably substituted or optionally unsubstituted phenyl, benzyl, naphthyl, biphenyl or anthracene groups, which preferably have at least 8 C atoms; the expression "alkenyl" can denote a $C_{2-10}$ alkenyl group, preferably a $C_{2-6}$ alkenyl group, which has the double bond(s) at any desired location and may be substituted or unsubstituted; the expression "alkynyl" can denote a $C_{2-10}$ alkynyl group, preferably a $C_{2-6}$ alkynyl group, which has the triple bond(s) at any desired location and may be substituted or unsubstituted; the expression "substituted" or substituent can denote any desired substitution by one or more, preferably one or two, alkyl, alkenyl, alkynyl, mono- or multi-valent acyl, alkanoyl, alkoxyalkanoyl or alkoxyalkyl groups; the afore-mentioned substituents may in turn have one or more (but preferably zero) alkyl, alkenyl, alkynyl, mono- or multi-valent acyl, alkanoyl, alkoxyalkanoyl or alkoxyalkyl groups as side groups; organic amines, amides, alcohols or acids, each having from 8 to 50 C atoms, preferably from 10 to 20 C atoms, can have the formulae $(alkyl)_2N$— or alkyl-NH—, —CO—$N(alkyl)_2$ or —CO—NH(alkyl), -alkyl-OH or -alkyl-COOH.

Despite an extended side chain function, the compounds of formula (12) can still bind to the active centre of the enzyme dipeptidyl peptidase IV and analogous enzymes but are no longer actively transported by the peptide transporter PepT1. The resulting reduced or greatly restricted transportability of the compounds according to the invention leads to local or site directed inhibition of DP IV and DP IV-like enzyme activity.

By extending/expanding the side chain modifications, for example beyond a number of seven carbon atoms, it is accordingly possible to obtain a dramatic reduction in transportability. With increasing spatial size of the side chains, there is a reduction in the transportability of the substances. By spatially and sterically expanding the side chains, for example beyond the atom group size of a monosubstituted phenyl radical, hydroxylamine radical or amino acid residue, it is possible according to the invention to modify or suppress the transportability of the target substances.

Preferred compounds of formula (12) are compounds, wherein the oligopeptides have chain lengths of from 3 to 15, especially from 4 to 10, amino acids, and/or the polyethylene glycols have molar masses of at least 250 g/mol, preferably of at least 1500 g/mol and up to 15 000 g/mol, and/or the optionally substituted organic amines, amides, alcohols, acids or aromatic compounds have at least 12 C atoms and preferably up to 30 C atoms.

The compounds of the present invention can be converted into and used as acid addition salts, especially pharmaceutically acceptable acid addition salts. The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of formulas (1) to (12) are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

The present invention further includes within its scope prodrugs of the compounds of this invention. In general, such prodrugs will be functional derivatives of the compounds which are readily convertible in vivo into the desired therapeutically active compound. Thus, in these cases, the use of the present invention shall encompass the treatment of the various disorders described with prodrug versions of one or more of the claimed compounds, which convert to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113 and DE 198 28 114, which are fully incorporated herein by reference.

Where the compounds or prodrugs according to this invention have at least one chiral center, they may accordingly exist as enantiomers. Where the compounds or prodrugs possess two or more chiral centers, they may additionally exist as diastereomers. It is to be understood that all such isomers and mixtures thereof are encompassed within the scope of the present invention. Furthermore, some of the crystalline forms of the compounds or prodrugs may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

DP IV is present in a wide variety of mammalian organs and tissues e.g. the intestinal brush-border (Gutschmidt S. et al., "In situ"—measurements of protein contents in the brush border region along rat jejunal yilli and their correlations with four enzyme activities. Histochemistry 1981, 72 (3), 467–79), exocrine epithelia, hepatocytes, renal tubuli, endothelia, myofibroblasts (Feller A. C. et al., A monoclonal antibody detecting dipeptidylpeptidase IV in human tissue. Virchows Arch. A, Pathol. Anat. Histopathol. 1986; 409

(2):263–73), nerve cells, lateral membranes of certain surface epithelia, e.g. Fallopian tube, uterus and vesicular gland, in the luminal cytoplasm of e.g., vesicular gland epithelium, and in mucous cells of Brunner's gland (Hartel S. et al., Dipeptidyl peptidase (DPP) IV in rat organs. Comparison of immunohistochemistry and activity histochemistry. Histochemistry 1988; 89 (2): 151–61), reproductive organs, e.g. cauda epididymis and ampulla, seminal vesicles and their secretions (Agrawal & Vanha-Perttula, Dipeptidyl peptidases in bovine reproductive organs and secretions. Int. J. Androl. 1986, 9 (6): 435–52). In human serum, two molecular forms of dipeptidyl peptidase are present (Krepela E. et al., Demonstration of two molecular forms of dipeptidyl peptidase IV in normal human serum. Physiol. Bohemoslov. 1983, 32 (6): 486–96). The serum high molecular weight form of DP IV is expressed on the surface of activated T cells (Duke-Cohan J. S. et al., Serum high molecular weight dipeptidyl peptidase IV (CD26) is similar to a novel antigen DPPT-L released from activated T cells. J. Immunol. 1996, 156 (5): 1714–21).

The compounds and prodrugs of the present invention, and their corresponding pharmaceutically acceptable acid addition salt forms are able to inhibit DP IV in vivo. In one embodiment of the present invention, all molecular forms, homologues and epitopes of DP IV from all mammalian tissues and organs, also of those, which are undiscovered yet, are intended to be embraced by the scope of this invention.

Among the rare group of proline-specific proteases, DP IV was originally believed to be the only membrane-bound enzyme specific for proline as the penultimate residue at the amino-terminus of the polypeptide chain. However, other molecules, even structurally non-homologous with the DP IV but bearing corresponding enzyme activity, have been identified recently. DP IV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (49). Further DP IV-like enzymes are disclosed in WO 01/19866, WO 02/04610 and WO 02/34900. WO 01/19866 discloses novel human dipeptidyl aminopeptidase (DPP8) with structural und functional similarities to DP IV and fibroblast activation protein (FAP). The dipeptidyl peptidase IV-like enzyme of WO 02/04610 is well known in the art. In the Gene Bank data base, this enzyme is registered as KIAA1492. In another preferred embodiment of the present invention, all molecular forms, homologues and epitopes of proteins comprising DP IV-like enzyme activity, from all mammalian tissues and organs, also of those, which are undiscovered yet, are intended to be embraced by the scope of this invention.

Diseases which characteristically demonstrate hyperglycemia include diseases such as Diabetes mellitus, Type I and II. Diabetes may generally be characterized as an insufficient hormone output by the pancreatic β-cells. Normally, these cells synthesize and secrete the hormone insulin. In Type I diabetes, this insufficiency is due to destruction of the beta cells by an autoimmune process. Type II diabetes is primarily due to a combination of beta cell deficiency and peripheral insulin resistance. In the diabetic patient, the number of beta cells is reduced so not only is there a concern regarding the ability of beta cells to synthesize and release physiological insulin, but there is also a concern surrounding the critical mass of these insulin producing pancreatic cells.

Loss of beta cells is known to occur with the presence of diabetes. With the loss of these insulin producing cells, there exists a strain on the endocrine function of the pancreas to produce, for example, insulin. With the loss in insulin output, pathological processes due to hyperglycemia can become exacerbated.

GLP-1 acts as an islet growth hormone by stimulating β-cell proliferation, cell mass increase and by promoting undifferentiated pancreatic cells in specialized cells of the islet of Langerhans. Such GLP-1 exposed pancreatic cells show improved secretion of insulin and glucagon (43; 44). The inventors have discovered that it is desirable to increase GLP-1's half-life to thereby facilitate reconstitution of the pancreatic beta cells. The inventors have also discovered a method whereby catabolism of GLP-1 maybe attenuated in order to improve reconstitution of the pancreatic cells.

The method of the present invention for treating hyperglycemia in a mammal, including but not limited to humans, comprises potentiating GLP-1's presence by inhibiting DP IV, or related enzyme activities, using an inhibitor of the enzyme. Oral administration of a DP IV-inhibitor may be preferable in most circumstances. However, other routes of administration are envisaged in the present invention. By inhibiting the DP IV enzyme activity, the half-life of the active form of GLP-1 will be appreciably extended and maintained under physiological conditions. The extended presence of active GLP-1, in particular in the pancreatic tissue, will facilitate the differentiation of pancreatic epithelial cells into pancreatic effector cells, like insulin producing β-cells. Moreover, prolonging GLP-1's physiologically active presence in pancreatic tissue will facilitate the regeneration of those β-cells which are already present but in need of repair. Surprisingly, this effect is only observable after repeated dosing (see example 2). Since withdrawal of the medication results in restoration of the prior metabolic state, subchronic or chronic dosing of the DP IV effector is needed to maintain the achieved improved glycemia. These repaired insulin producing cells can then effectively contribute to the correction and maintenance of normal physiological glycaemic levels.

In the present invention endogenous GLP-1 is synthesized and released in the normal physiological routes. Ingestion of a meal can stimulate the release of GLP-1. Alternatively, glucose or its analog can be given orally in the form of a pharmaceutically acceptable carrier (for example, a "sugar pill") in order to stimulate release of endogenous GLP-1. Such glucose may be taken, before, concurrently or following administration of the DP IV-inhibitors.

The present invention provides a method of preventing or treating a condition mediated by modulation of the DP IV or DP IV—like enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds and prodrugs of this invention, and their corresponding pharmaceutically acceptable acid addition salt forms, for the preparation of a medicament for the prevention or treatment of a condition mediated by modulation of the DP IV-activity in a subject. The compound may be administered to a patient by any conventional route of administration, including, but not limited to, intravenous, oral, subcutaneous, intramuscular, intradermal, parenteral and combinations thereof.

In a further illustrative embodiment, the present invention provides formulations for the compounds of formulas 1 to 12, and their corresponding pharmaceutically acceptable prodrugs and acid addition salt forms, in pharmaceutical compositions.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, being sought by a researcher, veterinarian, medical doctor or other clinician, which includes alleviation of the symptoms of the disease or disorder being treated.

As used herein, the term "composition" is intended to encompass a product comprising the claimed compounds in the therapeutically effective amounts, as well as any product which results, directly or indirectly, from combinations of the claimed compounds.

To prepare the pharmaceutical compositions used in this invention, one or more compounds of formulas 1 to 12, or their corresponding pharmaceutically acceptable prodrugs or acid addition salt forms, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed. If desired, tablets may be sugar coated or enteric coated by standard techniques. For parenterals the carrier will usually comprise sterile water, through other ingredients, for example, for purposes such as aiding solubility or for preservation, may be included.

Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per dosage unit, e.g., tablet, capsule, powder, injection, suppository, teaspoonful and the like, of from about 0.01 mg to about 1000 mg (preferably about 5 to about 500 mg) and may be given at a dosage of from about 0.1 to about 300 mg/kg bodyweight per day (preferably 1 to 50 mg/kg per day). The dosages, however, may be varied depending upon the requirement of the patients, the severity of the condition being treated and the compound being employed. The use of either daily administration or post-periodic dosing may be employed. Typically the dosage will be regulated by the physician based on the characteristics of the patient, his/her condition and the therapeutic effect desired.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is ideally mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is ideally dispersed evenly throughout the composition so that the composition may be readily subdivided into equally effective dosage forms such as tablets, pills and capsules. This solid preformulation composition may then be subdivided into unit dosage forms of the type described above containing from about 0.01 to about 1000 mg, preferably from about 5 to about 500 mg of the active ingredient of the present invention.

The tablets or pills of the novel composition can be advantageously coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

This liquid forms in which the novel compositions of the present invention may be advantageously incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991, fully incorporated herein by reference. The protecting groups may be removed at a convenient subsequent stage using methods known from the art.

The method of treating conditions modulated by dipeptidyl peptidase IV and DP IV—like enzymes described in the present invention may also be carried out using a pharmaceutical composition comprising one or more of the compounds as defined herein and a pharmaceutically acceptable carrier. The pharmaceutical composition may contain from about 0.01 mg to 1000 mg, preferably about 5 to about 500 mg, of the compound(s), and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds of the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen and dosage strength will need to be accordingly modified to obtain the desired therapeutic effects.

More preferably, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and other compounds known within the art.

The liquid forms are suitable in flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines using processes well described in the art.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamide-phenol, or polyethyl eneoxidepolyllysine substituted with palmitoyl residue. Furthermore, compounds of the present invention may be coupled to a class of biodegradable polymers useful in achieving controlled release of a drug, for example, polyacetic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, bioavailability due to the mode of administration, and the advancement of disease condition. In addition, factors associated with the particular patient being treated, including patient age, weight, diet and time of administration, should generally be considered in adjusting dosages.

The compounds or compositions of the present invention may be taken before a meal e.g. 1 hour, 30, 15 or 5 min before eating or drinking, while taking a meal or after a meal.

When taken while eating, the compounds or compositions of the present invention can be mixed into the meal or taken in a separate dosage form as described above.

DP IV-inhiIt will be readily understood by the skilled artisan that numerous alterations may be made to the examples and instructions given herein including the generation of different DP IV-inhibitors and alternate therapeutic compositions without departing from either the spirit or scope of the present invention. The following examples as described are not intended to be construed as limiting the scope of the present invention. Additional discussion follows in the Examples.

EXAMPLE 1

The DP IVDP IV-inhibitor P32/98 is actively transported via the PepT1 intestinal peptide transporter. The fast and active transport of P32/98 through the intestinal mucosa is responsible for its fast onset. The $t_{max}$ is a prerequisite for the efficient targeting of dipetidylpeptidase IV (DP IVDP IV). Oral administration of P32/98 results in a maximum target inhibition 15 to 20 min and 30 to 40 minutes after ingestion in rats and men, respectively. Therefore, the DP UVDP IV-inhibitor should be given 10–20 min prior to glucose or meal intake.

In the first-human study with P32/98, pharmacodynamic parameters like insulin concentration and GLP-1 concentration in the plasma and blood glucose were investigated in 36 healthy male volunteers. The oral dosing of P32/98 was in the following concentrations: 7.5 mg, 15 mg, 30 mg, 60 mg, 120 mg and 240 mg. The results of above pharmacodynamic parameters are summarized below in Table 1.

The 36 healthy male subjects were divided into 3 individual groups with each group containing 12 subjects. In each individual group 9 subjects received active drug P32/98 and 3 received placebo. The subjects receiving active drug were dosed twice, at different periods and at different strengths. The strengths of the P32/98 received within the groups were as follows: group I received 7.5 mg and 60 mg; group II received 15 mg and 120 mg; and group III received 30 mg and 240 mg. The subjects in all groups who were receiving placebo were given placebo at both dosing intervals.

A pre-study examination of the subjects was conducted within 3–14 days before their participation in the study. A second portion of the study comprised an experimental phase and entailed six single-dose treatments of ascending concentrations of P32/98, (periods 1 to 6; Table 2) which concluded with a follow up examination. Each subject participated in the pre-study and experimental phase, which were separated by a washout phase of at least 5 days. The follow-up examination was done at least 7 days after the last dose of study drug. The study procedures of the six periods were identical, except for the dose under investigation.

Methods

Oral glucose tolerance test ("OGTT"): Subjects were required to be in a fasting state for at least 12 hours and comply with a carbohydrate-rich diet 3 days before each OGTT. At each glucose tolerance test, subjects ingested 300 mL of a mono-/disaccharid solution equivalent to 75 g glucose (Dextro® O. G.-T, Boehringer Mannheim, FRG). Blood samples (1.2 mL into sodium fluoride tubes) were taken immediately prior to glucose intake and at 30, 60, 90 and 120 min thereafter. Any glucose concentration above 126 mg/dl (7.0 mmol/L) at 0 min and 120 min was considered to be in a pathological glucose tolerance state.

An extended OGTT was performed on Day 1 of each dosing period. Subjects ingested 300 mL of a mono-/disaccharid solution equivalent to 75 g glucose. Blood samples (1.2 mL) were taken at the following intervals: 1) 5 minutes prior to glucose intake; 2) at 5, 15, 30, 45, 60, 75, 90, 120, 150 and 180 min after glucose intake; 3) 4, 12, and 24 and 48 hours after glucose intake. Additionally other pharmacodynamic assessments that are well known in the art were taken.

Insulin: 4.7 ml blood was collected into 4.9 ml EDTA-tubes. Samples were centrifuged (1500 g, 10 min) and stored frozen at −70° C. until laboratory analysis.

Glucose: 1.2 ml blood was collected into 1.2 ml sodium fluoride tubes. Plasma samples were centrifuged at 1500 g for 10 min and stored frozen at −70° C. until laboratory analysis.

GLP-1: 2.7 ml blood was collected in EDTA tubes and placed on ice or refrigerated, to which a dipeptidyl peptidase IV-inhibitor was added. The inhibitor was prepared in advance by researchers. Blood was collected in tubes and centrifuged immediately at 1000 g for 10 min in refrigerated centrifuge or the blood was placed in ice and centrifuged within 1 hour and aliquoted into equal samples. Blood was stored in appropriate aliquots at −70° C. (to avoid multiple freezing/thawing cycles) until laboratory analysis.

Results

Active GLP-1 concentrations A dose-dependent effect of P32/98 compared to placebo was found. Overall individual concentrations varied between 2–68 pmol/l. Pre-dose group means were between 3.77±2.62 pmol/l and 6.67±9.43 pmol/l and increased by up to 4.22 and 7.66 pmol/l following use of a placebo, but by 11.6 pmol/l (15 mg) and 15.99 pmol/l (240 mg P32/98) following use of the inhibitor. If the relative mean increase is estimated from the absolute concentrations, active GLP-1 concentrations increased by approximately 200–300% after placebo treatment, but by approximately 300–400% following P32/98 treatment. The absolute increase in medians after 15–240 mg P32/98 was 2–3-fold higher compared with placebo and the 7.5-mg dose (see Table 3) and roughly indicated a dose-response relationship. An increase above pre-dose values was present up to approximately 3–4 hours relative to the P32/98 dose.

Insulin concentrations showed an overall individual range of values between 3.40 and 155.1 µIU/ml. Mean (±SD) pre-dose concentrations varied between 7.96±1.92 µIU/ml (30 mg) and 11.93±2.91 µIU/ml (60 mg P32/98). Following the ingestion of 75 g of glucose at 10 min post-dose P32/98/placebo, mean insulin concentrations increased by 30.12 µIU/ml (120 mg P32/98) to 56.92 µIU/ml (30-mg group) within 40–55 min. There was no apparent difference between placebo and the P32/98 dosing groups and, again, no evidence for a dose-dependent effect of P32/98. Interestingly, the absolute increase in insulin concentration was lowest in the two highest P32/98 dosing groups (see Table 3). The insulin concentrations were elevated for 3–4 hours in all study groups including placebo.

Glucose concentrations showed an overall range between 2.47 to 11.7 mmol/l in the fasted state, during OGGT or after meals across all study subjects. Mean pre-dose concentrations between 4.55±0.41 (15 mg) and 4.83±0.30 mmol/l (7.5 mg P32/98) closely matched each other and showed little variation. Mean maximum concentrations were reached within 40–55 min post-dose, i.e. within 30–45 min after the 75 g glucose dose. Absolute mean concentrations were highest in the two placebo and 7.5 mg P32/98 dosing groups. The lowest absolute means were obtained from the 15 mg, 60 mg and d-240 mg dosing groups. The corresponding mean changes ranged between 3.44 to 4.21 mmol/l and 1.71 to 3.41 mmol/l, respectively, and closely matched the medians provided in Table 4. Although no perfect dose-dependency was observed, these results indicate a lower increase in glucose concentrations with increasing doses from 15–240 mg of P32/98 compared with placebo.

TABLE 3

Maximum Changes in Pharmacodynamic Parameters (0–12 h, medians)

|  | Placebo (1–3) | 7.5 mg P32/98 | 15 mg P32/98 | 30 mg P32/98 | Placebo (4–6) | 60 mg P32/98 | 120 mg P32/98 | 240 mg P32/98 |
|---|---|---|---|---|---|---|---|---|
| GLP-1, active [pmol/l] | 3.90 0:25 h | 4.10 1:10 h | 10.00 0:25 h | 10.60 0:40 h | 5.30 0:40 | 12.20 0:25 h | 11.10 0:25 h | 14.50 0:25 h |

TABLE 3-continued

Maximum Changes in Pharmacodynamic Parameters (0–12 h, medians)

|  | Placebo (1–3) | 7.5 mg P32/98 | 15 mg P32/98 | 30 mg P32/98 | Placebo (4–6) | 60 mg P32/98 | 120 mg P32/98 | 240 mg P32/98 |
|---|---|---|---|---|---|---|---|---|
| insulin [μIU/ml] | 46.29 0:55 h | 41.86 0:55 h | 29.67 0:55 h | 59.84 0:40 h | 42.90 0:40 h | 43.35 0:40 h | 28.63 0:40 h | 33.36 0:40 h |
| glucose [mmol/l] | 3.43 0:55 h | 4.66 0:55 h | 2.43 0:55 h | 3.38 0:40h | 5.33 0:55 h | 2.92 0:40 h | 2.39 0:40 h | 1.73 0:40 h |

TABLE 4

Corrected $C_{max}$ and AUC of Glucose Concentrations 0–3 h After OGTT

|  | $AUC_{0\to 180\ min}$ [mmol * min/l] | | | $C_{max}$ [mmol] | | |
|---|---|---|---|---|---|---|
|  | Mean ± SD | Estimate[1] | 95%-CI | Mean ± SD | Estimate | 95%-CI |
| Periods 1–3 | | | | | | |
| Placebo | 223.9 ± 143.3 | | | 4.16 ± 1.10 | | |
| 7.5 mg P32/98 | 299.7 ± 111.4 | 75.8 | −48.1–199.7 | 4.94 ± 1.58 | 0.78 | −0.40–1.96 |
| 15 mg P32/98 | 130.9 ± 125.2 | −93.0 | −216.9–30.9 | 2.92 ± 1.10 | −1.24* | −2.43—0.06 |
| 30 mg P32/98 | 116.1 ± 134.0 | −107.7 | −231.6–16.2 | 3.26 ± 1.07 | −0.90 | −2.08–0.28 |
| Periods 4–6 | | | | | | |
| Placebo | 252.9 ± 103.3 | | | 4.91 ± 1.14 | | |
| 60 mg P32/98 | 151.8 ± 99.2 | −101.1 | −204.8–2.6 | 3.50 ± 1.66 | −1.41* | −2.66—0.17 |
| 120 mg P32/98 | 126.7 ± 147.3 | −126.1* | −229.8—22.4 | 3.09 ± 1.47 | −1.82** | −3.07—0.58 |
| 240 mg P32/98 | 24.7 ± 66.6 | −228.2*** | −331.8—124-5 | 1.99 ± 0.69 | −2.92*** | −4.16—1.68 |

[1]Results from ANOVA comparison versus placebo
*p < 0.05;
**p < 0.01;
***p < 0.001

Baseline-corrected mean peak ($C_{max}$) glucose concentrations exceeded 4.0 mmol/l in the two placebo and 7.5 mg P32/98 dosing groups only. These values were also below 3.0 mmol/l in the 15 mg and the 240 mg P32/98 treatment groups. The difference compared to placebo treatment was statistically significant for the 15 mg, 60 mg, 120 mg and 240 mg P32/98 dosing groups, but not for the 7.5 mg and the 30 mg dose groups. Mean baseline-corrected AUC values were >200 mmol*min/l after placebo and 7.5 mg P32/98, but clearly below 200 mmol*min/l following the 15 mg and 240 mg P32/98 doses. The reduction in systemic glucose exposition from the OGTT was statistically significant for the 15 mg, 60 mg, 120 mg and 240 mg P32/98 dosing groups, but not for the 7.5 mg and 30 mg dose groups (see Table 4). The evaluation of baseline-corrected values was very similar to those obtained from uncorrected data. Thus, the data indicated a clearly lower glucose exposition after the OGTT in P32/98 treated healthy subjects, which was an approximate, but not perfect dose-dependent indication.

Conclusions

Figure 2:
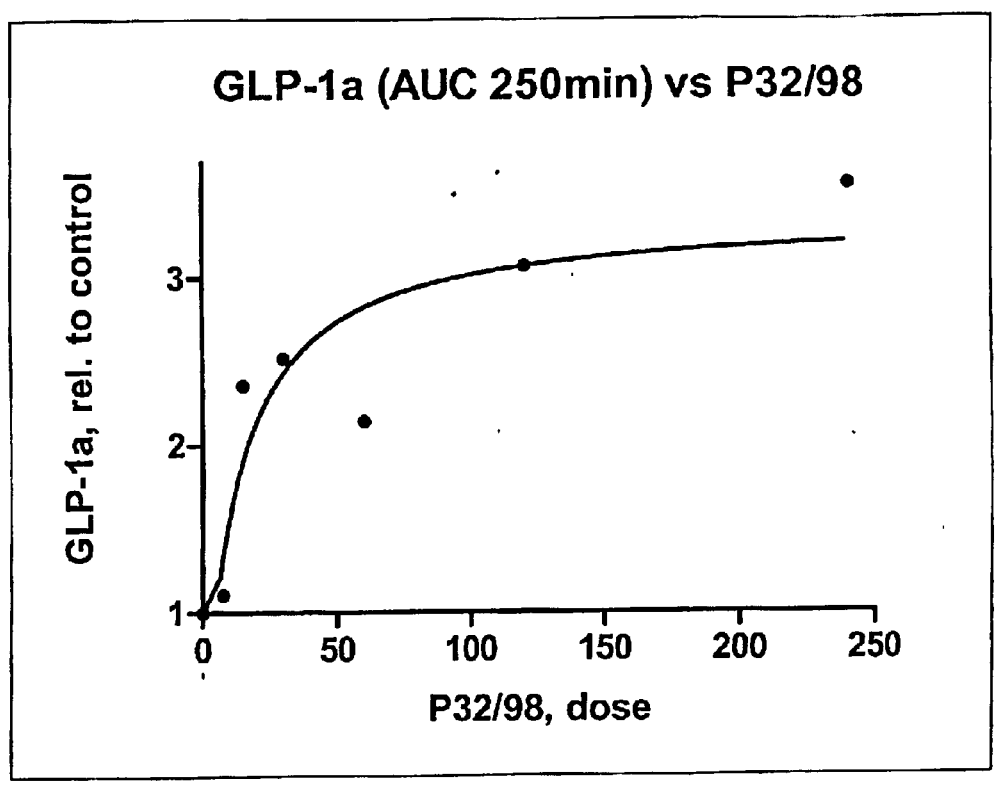
FIG. 2 is a graph representing the dependency of the AUC of circulating bioactive GLP-1 in humans (n=36) on the orally applied DP IV-inhibitor formulation P32/98.
Figure 3:
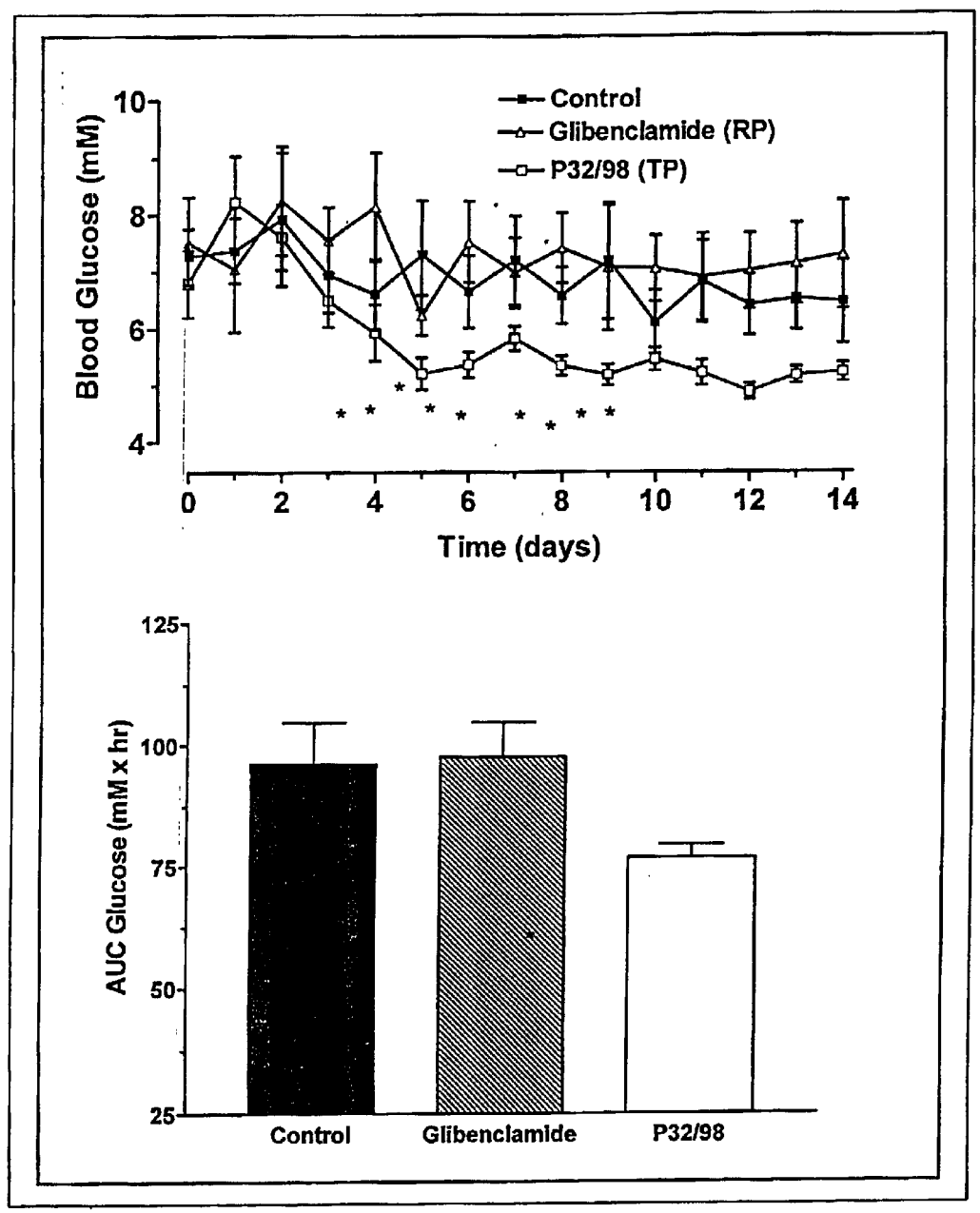
FIG. 3 is a graphical representation showing the improvement of morning blood-glucose (MBG) after subchronic monotherapeutic application of 8.7 mg/kg/d of P32/98 to obese, diabetic fa/fa rats.

Results of this study allow the following pharmacodynamic conclusions:

Active GLP-1 increased by approximately 300–400% following P32/98 treatment 10 min prior to OGTT, but no effect discernible from placebo treatment was seen for the 7.5-mg dose level (see FIGS. 1 and 2). Insulin concentrations appeared to be decreased at doses of 120–240 mg following stimulation with 75 g glucose. During the OGTT in healthy subjects, glucose concentrations showed a significantly lower increase after P32/98 treatment (15–240 mg) compared with placebo, which was related to the P32/98 dose.

EXAMPLE 2

In the obese Zucker rat, P32/98 nutrient-dependent supports initial insulin secretion. However, during a subchronic treatment, P32/98 reduces the total daily insulin secretion. Compared to a control glibenclamide, which increases insulin output by 27%, P32/98 causes an economization of insulin by saving 45% compared to the control.

Testing was undertaken to determine whether P32/98 is a prime candidate to influence glucose tolerance in vivo by increasing the circulating half-lifes of the incretins GIP and GLP-1. Comparative studies were carried out with glibenclamide (Maninil® Berlin-Chemie, Berlin, Germany) as reference substance, Glibenclamide is one of the most effective drugs for reducing blood glucose in Type 2 diabetic patients and one of the most frequently prescribed sulphonylureas.

Male Zucker fa/fa rats, which exhibit abnormalities in glucose metabolism and are a well established animal model for Type 2 diabetes, were investigated in the following way: P32/98 and glibenclamide were given once daily before food intake for a period of 21 days. The parameters monitored were morning blood glucose and plasma insulin levels. In a day-night profile, glycaemia and insulinaemia were monitored from day 16 to day, 17. An OGTT was performed finally on day 21 to monitor blood glucose and plasma insulin kinetics to assess changes in glucose tolerance. Glibenclamide (DAB 1996; R011150/33372) was donated by Berlin-Chemie (Berlin, Germany). Male Zucker (fa/fa) rats of the body weight class of 300 g were purchased from Charles River (Sulzfeld, Germany).

Methods

Housing Conditions: Animals were kept single-housed under conventional conditions with controlled temperature (22±2° C.) on a 12/12 hours light/dark cycle (light on at 06:00 a.m.). Standard pellets (ssniff®, Soest, Germany) and tap water acidified with HCl were allowed ad libitum, Catheterization of Carotid Artery: After one week of adaptation carotid catheters were implanted in the rats under general anesthesia (injection of 0.25 ml/kg i.p. Rompun® [2%], Bayer, Germany) and 0.5 ml/kg i.p. Velonarkon® (Arzneimittelwerk Dresden, Germany). The animals were allowed to recover for one week. The catheter was flushed with heparin-saline (100 IU/ml) three times per week.

Repeated Dosing: 30 male non-diabetic Wistar and 30 male diabetic Zucker rats were randomized to RP (Reference Product: glibenclamide)-, TP-(Test Product: P32/98) and CO-(Control) groups (N=10 per group). Thereafter, the non-diabetic Wistar rats were treated orally once daily with RP (5 mg/kg b.w.) or TP (21.61 mg/kg b.w.) and the diabetic Zucker rats were treated orally once daily with RP (1 mg/kg b.w.) or TP (21.61 mg/kg b.w.) for 21 days at 05.00 p.m. (before regular food intake in the dark phase). The controls were given 1% cellulose solution orally (5 ml/kg), Blood samples were taken every morning at 07.30 a.m. from tail veins for measurement of blood glucose and plasma insulin. The last blood samples of this part of the program were taken at 07.30 a.m. on the $15^{th}$ day to measure blood glucose and plasma insulin. The oral drug therapy was continued for one week. Recording the day-night profile under the above therapy blood glucose ($\Delta t=3$ h) and plasma insulin ($\Delta t=3–6$ h) were monitored from day 16 (at 05.00 p.m. beginning) to day 17 (at 02.00 p.m. end).

OGTT: A final OGTT was performed on day 21 with blood sampling from the tail vein. Blood samples from the tail vein were taken at −12 h (the night before day 21), at 0 min (immediately before the beginning of OGTT), at 10, 20, 30, 40, 50, 60, 80, 100 and 120 min. Blood samples were taken in 20 µl glass capillaries for blood glucose measurements and in Eppendorf tubes (100 µl). The latter were immediately centrifuged and the plasma fractions were stored at −20° C. for insulin analysis.

Blood glucose: Glucose levels were measured using the glucose oxidase procedure (Super G Glukosemeβgerät; Dr. Müller Gerätebau, Freital, Germany).

Plasma insulin: Insulin concentrations were assayed by the antibody RIA method (LINCO Research, Inc. St. Charles, Mo., USA).

Results

Figure 4A:
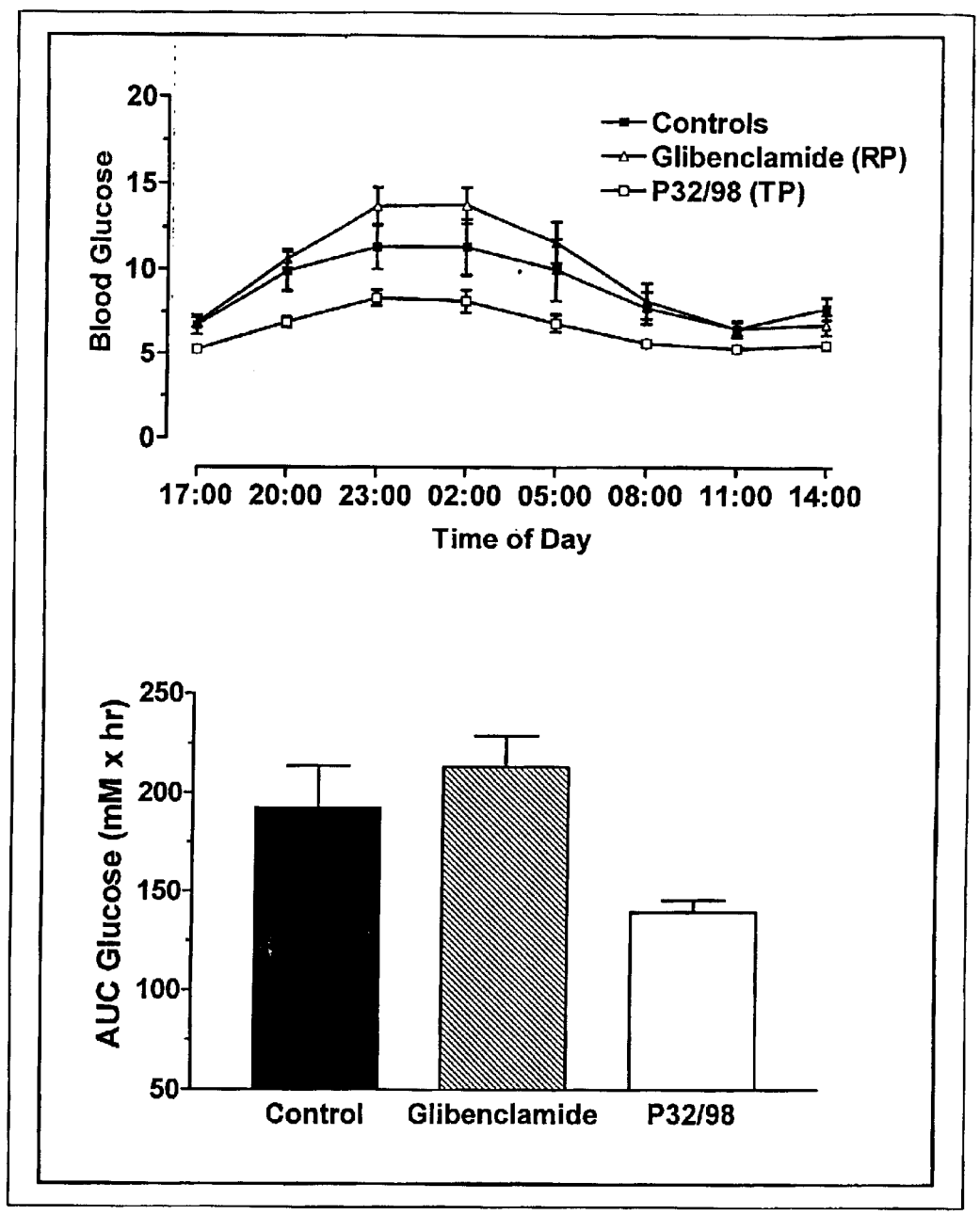
FIG. 4a is a graphical representation showing improved glucose-control due to DP IV-inhibitor treatment after 16-days of treatment in obese diabetic rats

Day-night profile of glycemia (see FIG. 4A): The mean blood glucose concentration in the CO-group on day 16 was 7.78±0.83 mmol/l before drug application at 05.00 p.m. After oral placebo ingestion and food intake in the dark phase, glycemia increased to maximum values of 12.18±1.34 mmol/l at 11.00 p.m. Thereafter, glycemia declined very slowly to the lowest values of 7.27±0.61 mmol/l at 11 a.m., followed by an increase to 8.90±0.92 mmol/l at 02.00 p.m. next day. In the RP-group, a similar picture of glycemia was seen. However, from a comparable mean value of 7.96±1.13 mmol/l at 05.00 p.m. with respect to control animals there was a stronger increase to 14.80±1.46 mmol/l (11.00 p.m.) and thereafter a decline to 7.66±1.22 mmol/l (11.00 a.m.) and a further slight reduction to 7.34±0.77 mmol/l at 02.00 p.m. of the next day, respectively. In the TP-group the Zucker rats had a normal mean blood glucose value of 5.25±0.16 mmol/l at 05.00 p.m. and the individual values were in the range from 4.34 to 6.07 mmol/l. Glycemia showed an increase of about 3 mmol/l to 8.34±0.47 mmol/l at 11.00 p.m. This was followed by a permanent decline to basal values which were reached at 08.00 a.m. (5.64±0.23) and which were maintained at 11.00 a.m. (5.33±0.14 mmol/l) and 02.00 p.m. next day (5,51±0.19 mmol/l), respectively.

Figure 4B:
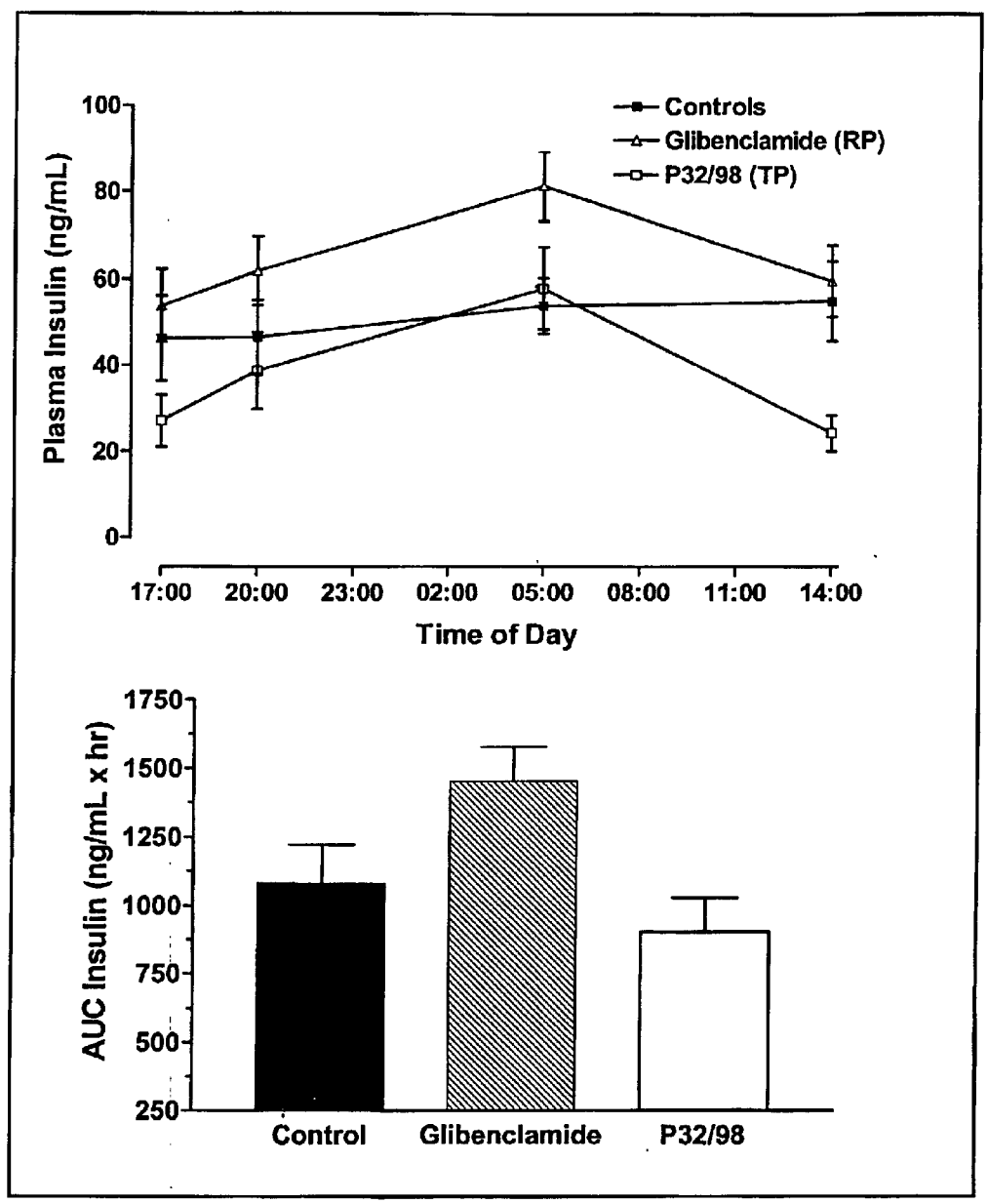
FIG. 4b is a graphical representation showing reduced insulin-secretion due to DP IV-inhibitor treatment after 16 days of treatment in obese diabetic rats.

Day-night profile of insulinemia: (see FIG. 4B): The CO- and RP-Zucker rats were strongly hyperinsulinemic. Insulin showed a variability in mean values at 05.00 p.m. in the CO-group (47.0±8.7 ng/ml), 08.00 p.m. (45.5±7.7 ng/ml), 05.00 a.m. (54.2±5.7 ng/ml) and 02.00 p.m. next day (61.0±10.2 ng/ml; NS) which showed no relation to the excursions of blood glucose. In RP-group in the dark phase from 06.00 p.m. to 06.00 a.m. there, was a significant increase in plasma insulin values with a maximum at 5.00 a.m. This parameter increased from strongly hyperinsulinemic values of 50.0±8.2 ng/ml (05.00 p.m.) via 57.3±8.2 ng/ml (08.00 p.m.) to 76.3±8.6 ng/ml (05.00 a.m.; p<0.01 vs. initial value), which was followed by a decline to 58.3±7.3 ng/ml (02.00 p.m. the next day). In this RP-group insulin was strongly phase shifted in relation to the blood glucose excursions. In the TP-group, the Zucker rats were also hyperinsulinemic. Plasma insulin at 05.00 p.m. was significantly lower than in the RP (p<0.05 vs. RP). Parallel to blood glucose increases (FIG. IV/3 A) there was an increase in plasma insulin at 08.00 p.m. (41.9±8.5 ng/ml). The maximum insulin value was measured at 05.00 a.m. (57.1±8.6 ng/ml; p<0.01 vs. initial values). The concentration of plasma insulin was lowered reaching basal concentration (24.3±3.7 ng/ml) at ca. 2.00 p.m. the next day which was significantly lower than in CO or RPgroups (p<0.01 vs. CO or TP).

Figure 5A:
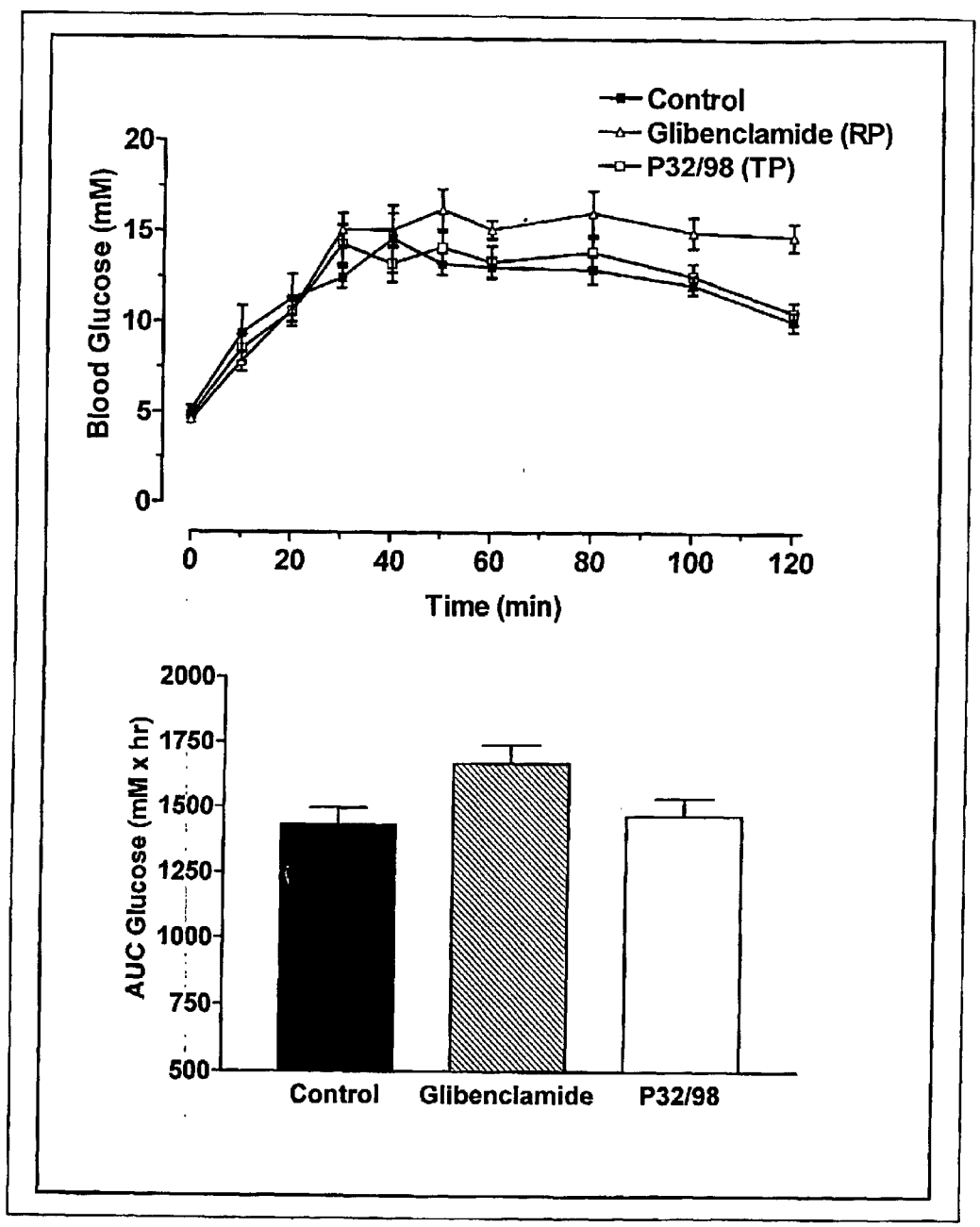
FIG. 5a is a graphical representation showing the blood glucose levels as a function of time in the maintenance of improved glycemia after 21 days of subchronic treatment of obese, diabetic fa/fa rats by the formulated DP IV-inhibitor P32/98.

OGTT after 21 days treatment, blood glucose curves (See FIG. 5A): The last drug application at 05.00 p.m. and overnight fasting on day 21 were followed by a significant decline in glycemia in the CO-group from 8.68±1.26 mmol/l (05.00 p.m.) to 5.08±0.24 mmol/l (p<0.05), in the RPgroup from 8.81±1.21 mmol/l to 4.91±0.37 mmol/l (p<0.01) and in the TP-group from 5.75±0.23 mmol/l to 4.88±0.13 mmol/l (p<0.01). For this reason oral glucose loads were performed from a comparable basal glucose concentration level in all three experimental groups found in the morning (07.30 a.m.).

In the CO-group glycemia increased after oral glucose application to peak values of 14.64±1.42 mmol/l within 40 min, Later there was a slight, significant decline to 9.75±0.46 mmol/l at the end of the test (120 min). In the RP-group, there was a steep increase to higher blood glucose values of 16.33±0.98 and 16.24±1.09 mmol/l at 50 min and 80 min, respectively. The high glucose concentrations were maintained until the end of study at 120 min (100 min: 15.13±0.76 mmol/l, 120 min: 14.81±0.66 mmol/l; NS from the former peak values). In the TP-group, similar properties of the mean blood glucose curve as in the CO-group were found. Glycemia increased to 14.54±0.65 mmol/l at 50 min and declined significantly to a value of 10.67±0.62 mmol/l (120 min; NS from CO).

The glucose area under the curve (G-AUC$_{0-120\ min}$) in the CO- and TP-groups were 823±41 and 895±50 mmol·min/l, respectively (NS). In the RP-group this parameter was determined as 1096±76 mmol-min/l and that value was significantly higher than in CO-(p<0.01) or TP-groups (p<0.05).

Figure 5B:
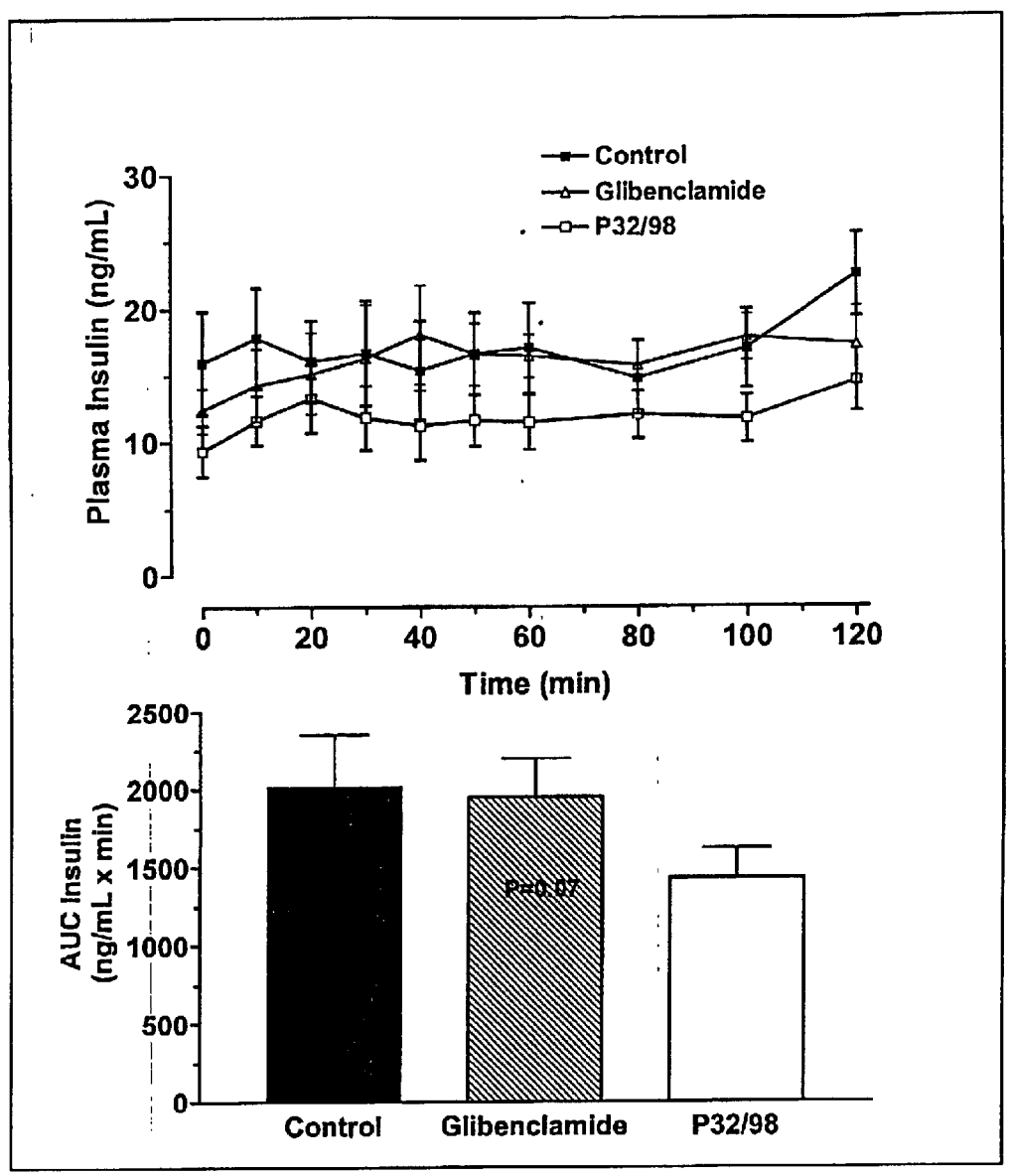
FIG. 5b is a graphical representation showing the plasma insulin levels as a function of time in the maintenance of improved glycemia after 21 days of sub-chronic treatment of obese, diabetic fa/fa rats by the formulated DP IV-inhibitor P32/98.

OGTT after 21 days treatment, plasma insulin (See FIG. 5B): Overnight fasting in the Zucker rats led to reduced plasma insulin concentrations in the CO-animals (14.6±3.7 ng/ml), in the RP-group to 11.8±1.5 ng/ml, and in the TP-group to 9.3±1.5 ng/ml, respectively. The differences between experimental groups were not significant. After a glucose stimulus, plasma insulin remained mostly unchanged in the CO-, RP- and TP-groups. Slightly higher values were found at 120 min in the CO-group only, amounting to 21.3±3.0 ng/ml, which was significantly higher than in the TP-group (p<0.05). The I-AUC$_{0-120\ min}$ was generally low. In the TP-group this parameter was lower than in the CO- or RP-groups (NS).

Summary

Morning blood glucose: The placebo treated controls were hyperglycaemic (about 7.5 mmol/l). The mean concentration was unchanged during the study. RP therapy increased blood glucose by about 1.5 mmol/l within two days. Glycemia remained in the higher range. TP-medication reduced blood glucose to a normal value within 5 days. Blood glucose remained in the normal range up to the end of the study.

Plasma insulin: The control Zucker rats were hyperinsulinemic and showed some further insulin increase during the 14 days of observation. The RP-treated Zucker rats showed an insulin increase to significantly higher concentrations than in control animals. The TP application did slightly decrease insulin concentration for 14 days in comparison to the control animals.

OGTT after 21 days treatment, blood glucose: Overnight fasting reduced blood glucose to normal values in the experimental groups. The placebo-treated animals showed about a 9 mmol/l blood glucose increase within 40 min after the glucose load and a slight decline thereafter. RP-treated Zucker rats showed about 11 mmol/l blood glucose increase after the glucose load with no decline during the test. The mean blood glucose curve of the TP-treated animals was not different from that of the controls. The RP-treatment increased the G-AUC; the TP-medication did not increase G-AUC in comparison to the placebo application.

OGTT after 21 days treatment, plasma insulin: The control Zucker rats had the highest fasting insulin of the three experimental groups of about 15 ng/ml. After the glucose load, insulin increased significantly only at the end of the test (120 min). The RP-treated rats had some lower fasting insulin of ~12.5 ng/ml at the beginning of the OGTT and an earlier increase at 40 min with no decline at the end of the test. The TP-treated rats had the lowest fasting insulin of ~9 ng/ml at the beginning of the OGTT, an early modest increase at 20 min in relation to the blood glucose rising and lowered concentrations between 40 min and 100 min. The I-AUC was slightly lower in the TP-treated rats.

Conclusion

The DP IV-inhibitor P32/98 (TP), given once daily, normalized morning blood glucose, reduced hyperinsulinemia, held blood glucose in the day-night profile below the (for diabetic patients) critical 8.3 mmol/l. The metabolic benefit was retained a limited time after cessation of P32/98 medication.

EXAMPLE 3

Two groups of Vancouver diabetic Fatty (VDF) rats (a sub-strain of the fatty fa/fa Zucker rat that display abnormalities characteristic of type II diabetes including mild hyperglycemia, hyperinsulinemia, glucose intolerance, hyperlipidemia, impaired insulin secretion, and peripheral and hepatic insulin resistance) (n=6) were treated p.o. twice daily for three months with the DP IV-inhibitor P32/98 (20 mg/kg/day). Parameters including body weight, food and water intake, and oral glucose tolerance were regularly examined to track the progression of the disease and to study the possible therapeutic effects of the inhibitor. At the end of the treatment period, ex vivo fat and muscle insulin sensitivity were assessed, and pancreas perfusion was performed to measure β-cell glucose responsiveness. Monthly oral glucose tolerance tests (OGTT), performed after drug washout, revealed a progressive and sustained improvement in glucose tolerance in the treated animals. After twelve weeks of treatment, peak OGTT blood glucose values in the treated animals averaged 8.5 mM less than in the controls (12.0±0.7 mM vs, 20.5±1.3 mM, respectively). Also, concomitant insulin determinations showed an increased early phase insulin response in the treated group (43% increase). Further, whereas control pancreata failed to respond to an 8.8 mM glucose perfusion, pancreata from treated animals exhibited a 3.2-fold rise in insulin secretion, indicating enhanced β-cell glucose responsiveness. Also, both basal and insulin-stimulated glucose uptake were increased in soleus muscle strips from the treated group (20% and 50% respectively), providing direct evidence for an improvement in peripheral insulin sensitivity. As will be seen in the following examples, long-term DP IV-inhibitor treatment was shown to cause sustained improvements in glucose tolerance, insulinemia, β-cell glucose responsiveness and peripheral insulin sensitivity, novel effects which support the use of DP IV-inhibitors in the treatment of diabetes.

Materials and Methods

Materials. The DP IV-inhibitor P32/98 (Di-[2S,3S]-2-Amino-3-methyl-pentanoic-1,3-thiazolidine fumarate) was synthesized as previously described (22).

Animals. Six pairs of male fatty (fa/fa) VDF Zucker rat littermates were randomly assigned to either a control or treatment (P32/98) group at 440 g body weight (11±0.5 weeks of age). Animals were housed on a 12 hour light/dark cycle (lights on at 6 am) and allowed access to standard rat food, and water ad libitum.

Protocol for daily monitoring and drug administration. The treatment group received P32/98 (10 mg/kg) by oral gavage twice daily (0800 h and 1700 h) for 100 days, while the control animals received concurrent doses of vehicle consisting of a 1% cellulose solution. Every two days, body weight, morning and evening blood glucose, and food and water intake were assessed. Blood samples were acquired from the tail, and glucose measured using a SureStep analyzer (Lifescan Canada Ltd., Burnaby). Food and water intake were measured by subtraction.

Protocol for monthly assessment of glucose tolerance. Every four weeks from the start of the experiment an oral glucose tolerance test (OGTT; 1 g/kg) was performed after an 18 hour fast and complete drug washout (~12 circulating half-lives for P32/93). No 0800 h dose was administered in this case, Blood samples (250 µl) were collected from the tail using heparinized capillary tubes, centrifuged and stored at −20° C. In the case of the 12 week OGTT, blood was collected directly into tubes containing the DP IV-inhibitor P32/98 (final concentration 10 µM) for analysis of active GLP-1 (EGLP-35K; Linco Research Inc., USA). Plasma insulin was measured by radioimmunoassay using a guinea pig anti-insulin antibody (GP-01) as previously described (23), and blood glucose was measured as described above. Plasma DP IV-activity was determined using a calorimetric assay measuring the liberation of p-nitroanilide ($A_{405\ nm}$) from the DP IV substrate H-Gly-Pro-pNA (Sigma; Parkville, ON). It is important to note that the assay involves a 20-fold sample dilution and therefore underestimates the actual degree of inhibition occurring in the undiluted sample when using rapidly reversible inhibitors such as P32/98.

Estimation of insulin sensitivity made from OGTT data was performed using the composite insulin sensitivity index (CISI) proposed by Matsuda and DeFronzo (24). Calculation of the index were made according to the equation, $$CISI = 10,000/((FPG \times FPI) \times (MG \times MI))^{1/2} \qquad \text{Eq. 1}$$

where FPG and FPI were fasting plasma glucose and insulin concentrations respectively and MG and MI were the mean glucose and insulin concentrations over the course of the OGTT.

Protocol for 24 hour glucose, insulin and DP IV profile. In order to determine the effects of DP IV-inhibition over a 24 hour period, blood glucose, insulin, and DP IV-activity levels were measured as described above, every three hours for 24 hours, six weeks into the study. Drug dosing was continued at the appropriate times during the profile.

Skeletal muscle insulin sensitivity. Uptake of $^{14}C$-labeled glucose in soleus muscle strips was measured as an indicator of skeletal muscle insulin sensitivity. In brief, after an overnight fast and 18 hours after the last dose of P32/98, the animals were anesthetized with sodium pentobarbital (Somnotol; ~50 mg/kg). The soleus muscles of both hindlimbs were exposed and isolated. After freeing the muscle by severing the proximal and distal tendons, strips of approximately 25–35 mg were pulled from the muscle (the two, outer-thirds of each muscle were used). After weighing, the strips were fixed onto stainless steel clips at their resting length, and allowed to stabilize for thirty minutes in a Krebs-Ringer bicarbonate buffer supplemented with 3 mM pyruvate, continuously gassed with 95% $O_2$:5% $CO_2$ and held at 37° C. in a shaking water bath. These conditions were maintained for the duration of the experiment unless otherwise stated, In order to assess glucose uptake in response to insulin, muscle strips underwent two preincubations (30 and 60 minutes respectively) followed by a half-hour test incubation. Both the second preincubation and the test incubation contained either 0, or 800 µU/ml insulin. The test incubation was performed in media supplemented with [$^3H$]-insulin (0.1 µCi/ml) as a measure of extracellular space, and the non-metabolizable glucose analogue [$^{14}C$]-3-O-methylglucose (0.05 µCi/ml) for measurement of glucose uptake. After incubation, each strip was blotted dry, digested with proteinase K (0.25 µg/ml) and the radioactivity of the muscle digests measured with a liquid-scintillation-counting dual-isotopic program.

Adipose tissue insulin sensitivity. To estimate insulin sensitivity in adipose tissue, glycogen synthase (GS) and acetyl-CoA carboxylase (ACC) levels were measured as previously described (25, 26). In brief, 3 $cm^3$ samples of ependymal adipose tissue were obtained from anaesthetized animals and subjected to a 16 minute collagenase digestion (0.5 mg/ml). Recovered adipocytes were washed three times, and allowed to stabilize for one hour in 37° C. Krebs buffer repetitively gassed with 95% $O_2$: 5% $CO_2$. Two milliliter aliquots of the adipocyte suspension containing 0, 100, 250, 800, and 1500 µU/ml insulin were incubated for 30 minutes and immediately flash frozen on liquid nitrogen and stored at –70° C. Prior to ACC and GS assessment, stored samples were thawed, homogenized in buffer pH 7.2 containing 20 mM MOPS, 250 mM sucrose, 2 mM EDTA, 2 mM EGTA, 2.5 mM Benzamidine, pH 7.2), and centrifuged (15 min @ 15,000×g).

For measurement of ACC activity, 50 µl aliquots of supernatant, preincubated in the presence or absence of 20 mM citrate, were added to 450 µl of [$^{14}C$]-$HCO_3$ containing assay buffer pH 7.4 (50 mM HEPES, 10 mM $MgSO_4$, 5 mM EDTA, 5.9 mM ATP, 7.8 mM glutathione, 2 mg/ml BSA, 15 mM $KHCO_3$ and 150 µM Acetyl CoA). After three minutes, the reaction was arrested by the addition of 200 µl of 5 M HCl. Samples were dried for 6 hours, resuspended in 400 µl of distilled water, combined with 3 mls of scintillation cocktail and counted on a Beckman LS 6001C β-counter. GS activity was measured using a modification of a filter paper method (26): 25 µl of the cell extracts prepared as indicated above were added to assay buffer pH 7.0 (75 mM MOPS, 75 mM NaF, 10 mg/ml glycogen, 2 mM UDP-[$^{14}C$]-glucose) held at 30° C. in the presence or absence of 15 mM glucose-6-phosphate. Each reaction was stopped by spotting 50 µl of the reaction mixture onto Whatmann 3MM filter paper and immersing the paper in 66% ethanol. After three ethanol washes, the samples were air-dried and the [$^{14}C$] activity (UDP-[$^{14}C$]-glucose incorporation into glycogen) determined.

Protocol for pancreas perfusion. After excision of soleus and ependymal adipose tissue samples, the pancreas was isolated and perfused with a low-to-high glucose (4.4 mM to 8.8 mM) perfusion protocol as previously described (27). Following exposure through a mid-line incision on the ventral aspect, the pancreas was isolated, all minor vessels ligated, and a glucose perfusate introduced through the celiac artery. Perfusion effluent was collected at 1 minute intervals via the portal vein with a perfusion rate of 4 ml/min. Samples were stored at –20° C. until analysis.

Immunohistochemistry and β-cell mass determination. Pancreata were removed from anesthetized animals (50 mg/kg sodium pentobarbital) and placed directly into fixative for 48 hours (44% formaldehyde, 47% distilled $H_2O$, 9% glacial acetic acid). After paraffin embedding, 5 µm tissue sections were cut, mounted onto slides, and dried ready for staining. In order to assess β-cell area, sections were stained with a guinea pig anti-insulin primary antibody followed by peroxidase conjugated goat anti-guinea pig secondary. Slides were developed using diamonobenzidine and counterstained with hematoxylin. Analyses were performed using Northern Eclipse Software (Empix Imaging, Mississauga, ON, Canada) as previously described (28).

Statistical Analysis. Student's t-test and ANOVA were used, where appropriate, to test statistical significance of the data (P<0.05). Analysis was performed using Prism 3.0 data analysis software (GraphPad Software Inc., CA).

EXAMPLE 4

Effects of P32/98 treatment on body weight, daily blood glucose and food and water intake. VDF rats treated with P32/98 displayed a 12.5% (25 g) reduction in weight gain over the three month treatment period (control: 211±8 g; treated: 176±6 g) (FIG. 6A). Measurements of food and water intake revealed a minor decrease in water intake (FIG. 6B) in the treated animals concomitant with unaltered food intake. Food intake over the course of the experiment averaged 30.0±0.4 g/rat/day and 30.4±0.3 g/rat/day in the treated and control groups respectively. Food and water intake decreased over the course of the experiment paralleling the decrease in the rate of weight gain as the growth of the animals began to plateau at around 600–650 grams (data not shown). Bi-daily monitoring of blood glucose revealed no difference in morning or evening blood glucose values between the experimental groups, though neither group displayed notably hyperglycaemic values (data not shown). Morning blood glucose levels over the course of the experiment averaged 5.0±0.1 mM in the treated and 5.3±0.1 mM in the control animals. Evening blood glucose values averaged 6.7±0.1 mM and 7.0±0.2 mM respectively. Hematocrit, measured at four week intervals, indicated no adverse effects of the blood sampling protocol employed, averaging between 43.4% and 45.3% in both groups.

EXAMPLE 5

Effects of P32/98 treatment on blood glucose, insulin and DP IV levels over 24 hours. After six weeks of treatment a 24-hour profile of blood glucose, insulin and DP IV-activity levels was obtained by taking blood samples at 3 hr intervals, interrupting neither treatment administration nor the light/dark cycle. The profile confirmed that administration of P32/98 caused significant inhibition of DP IV-activity over the majority of the 24-hour cycle, with at least 65% inhibition during the feeding cycle (FIG. 7A). The integrated blood glucose excursion in the treated animals was 75% that of the controls, peaking at 7.7±0.3 mM as compared to 9.8±0.6 mM for the untreated animals (FIG. 7B). The corresponding plasma insulin profile exhibited not only a decrease in peak insulin values, but also of "basal", non-feeding, values (~0800 to 1800 h) in the treated animals (FIG. 7C).

EXAMPLE 6

Effects of P32/98 treatment on oral glucose tolerance. Three oral glucose tolerance tests, performed in the absence of circulating P32/98 and at one month intervals, were used to monitor the progression of the disease state in the control animals and to document any improvements displayed in the treated group. The initial oral glucose tolerance test, administered after four weeks of treatment, showed significant decreases (~2 mM) in basal, 45, 60, and 90 minute blood glucose values in the treated group despite overlapping plasma insulin excursions (FIG. 8A). Data from the second OGTT were very similar to the first; with the exception that the 120 min blood glucose value was also significantly lowered in the treated group (10.8±0.8 vs. 12.3±0.8 for the control animals); once again the insulin profiles were super imposable (data not shown). The final OGTT, performed after 12 weeks of treatment, showed a marked difference in glucose tolerance between the two groups with significantly decreased blood glucose values observed at all time points. Peak blood glucose values in the treated grouped averaged 12.0±0.7 mM, 8.5 mM less than that of the control animals (FIG. 8B), while two hour values in the treated group had returned to 9.2±0.5 mM, a 40% reduction compared to the controls. Active GLP-1 levels (GLP-1a), measured during the final OGTT using an N-terminally directed ELISA, were found to be unchanged (FIG. 8B). Despite this lack of altered GLP-1a levels, the early phase insulin response measured in the treated group exceeded that of the control animals by 43%. However, the integrated insulin responses between the two groups showed no significant difference. Analysis of the OGTT data using the composite insulin sensitivity index of Matsuda and DeFronzo (24), revealed a progressive increase in estimated insulin sensitivity of the treated animals relative to the controls (FIG. 8C).

Figure 9:
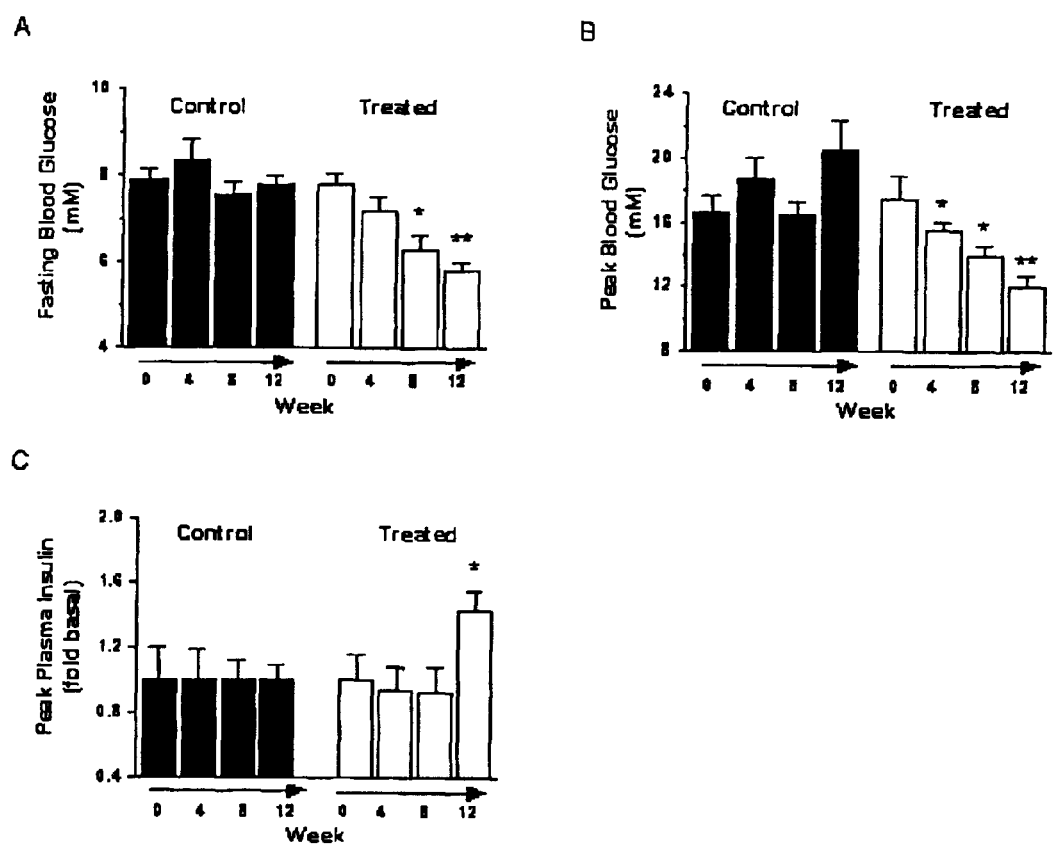
FIG. 9 shows a comparison of fasting (A) and peak (B) blood glucose and peak plasma insulin (C), DP IV-actmeasured during OGTTs performed at four week intervals in control (solid squares) or DP IV-inhibitor treated (open circles) VDF rats (n=6). Statistical significance (p<0.05) is indicated by an asterisk.

Comparison of the oral glucose tolerance tests over the course of the experiment revealed a progressive decrease in both fasting and peak blood glucose values in animals treated with P32/98, improvements that were not observed in the control animals (FIGS. 9 A&B). Peak insulin values did not differ significantly between the two experimental groups until the final, 12 week, OGTT, at which time the peak insulin levels in the treated animals exceeded those of the control animals by an average of 43% (FIG. 9C). Plasma DP IV-activity, measured at the start of each OGTT, was significantly increased in the treated group by week 8 of the study and the elevation maintained at week 12 (FIG. 9D).

EXAMPLE 7

Figure 10:
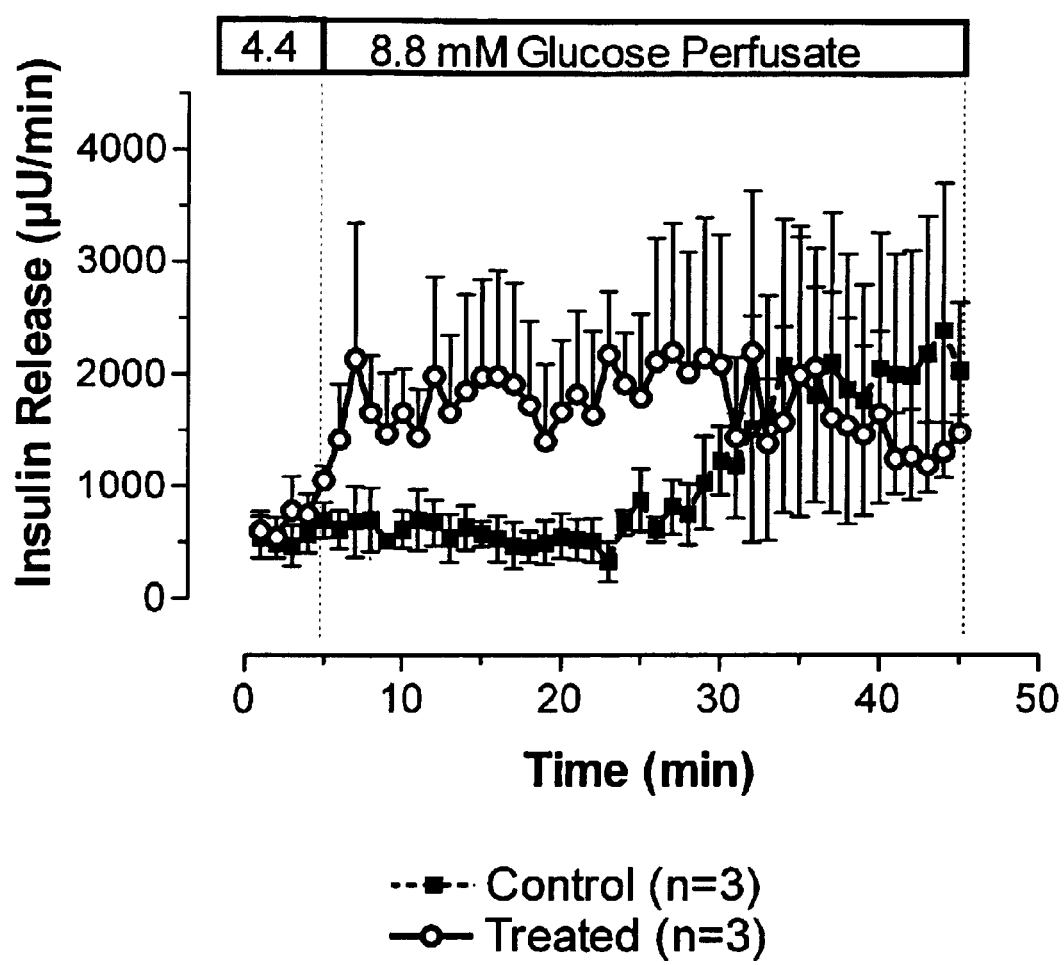
FIG. 10 shows insulin release measured during perfusion of pancreata from VDF rats after three months of treatment with (open circles) or without (solid squares) the DP IV-inhibitor P32/98 (n=3)

Effects of chronic DP IV-inhibitor treatment on pancreatic glucose responsiveness. A low-to-high step glucose perfusion protocol was performed on the pancreata of half of each group of animals. The shift from 4.4 to 8.8 mM glucose perfusate caused a 3.2-fold increase in insulin secretory rate in the pancreata from the treated animals (FIG. 10). The insulin secretory rate shifted from a basal 570±170 µU/min to over 2100 µU/min within two minutes of high glucose perfusion. The same glucose step procedure failed to elicit any significant response in the control pancreata until well over twenty minutes of high glucose perfusion (FIG. 10).

EXAMPLE 8

Effects of chronic DP IV-inhibitor treatment on muscle and fat insulin sensitivity. To further define the apparent improvements in insulin sensitivity observed in the OGTT data, assays of muscle and fat insulin sensitivity were performed. Glycogen synthase (GS) and acetyl coA carboxylase (ACC) activity were measured in isolated adipocytes along with uptake of $^{14}C$-labelled glucose into soleus muscle strips. ACC levels in adipose from both experimental groups were minimal (approaching limits of detection), lacked insulin responsiveness, and showed no difference between the two groups (data not shown). GS activity also appeared insensitive to insulin, though the activity of the enzyme at all measured insulin concentrations was higher in the treated animals than in their control littermates (FIG. 11A). Soleus muscle strips taken from the treated animals exhibited significantly higher rates of glucose uptake both in the basal and in the insulin stimulated state. Glucose uptake in the non-stimulated state was 22% higher in the treated rats (FIG. 11B). The insulin-stimulated rise in glucose uptake was enhanced in the treated group compared to the controls (control: 58.5±3.5; treated: 87.5±10.4 cpm/mg tissue at 800 µU/ml insulin).

EXAMPLE 9

Effects of chronic DP IV-inhibitor treatment on β-cell area and islet morphology. The three month oral DP IV-inhibitor regimen yielded no significant differences in β-cell area, or islet morphology. Islets from control and treated animals comprised 1.51±0.04% and 1.50±0.03% of the total pancreatic area, respectively. Large, irregularly shaped islets with significant β-cell hyperplasia were observed in both groups, morphology characteristic of the fa/fa Zucker rat.

EXAMPLE 10

Processing of bioactive peptides by DP IV Matrix-assisted laser desorption/ionisation mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. The spectrometer was calibrated externally. The best signal reproducibility and no alkali-adduct-signals were found using a matrix solution of 30 mg 2'-6'-dihydroxyacetophenone (Aldrich) and 44 mg diammonium-hydrogencitrate (Fluka) in acetonirile/0.1% TFA (1/1). To obtain spectra of peptides by the treatment of purified DP IV or human plasma in the presence or absence of the specific DP IV-inhibitor P 32/98, substrates were incubated at 37° C. with 40 mM tricine/HCl buffer pH 7.6 and either enzyme solution or serum in a 2:2:1 ratio. Samples of the reaction mixtures were removed at various time intervals and mixed with equal volumes of the matrix solution. By mixing assay sample and matrix, the low pH of the matrix solution stopped the enzymatic reaction. A small volume (<1 µl) of this mixture was transferred to a probe tip and immediately evaporated in a Hewlett-Packard G2024A Sample Prep Accessory to ensure rapid and homogenous sample crystallization. All spectra were generated using automatic mode by averaging 250 single shots selected by the signal-to-noise ratio.

All peptides were purchased by BACHEM. In incubation solutions the concentration of substrates was 25 $\mu$Mol/l. The DP IV used in this study was purified from porcine kidney. The specific activity measured using Gly-Pro-4-nitroanilide as a chromogenic substrate was at least 5 units/mg. In the case of plasma, fresh prepared human EDTA-plasma from healthy subjects was used. The concentration of the specific DP IV-inhibitor isoleucyl thiazolidine hemifumarate in the incubation solutions was 9.8 $\mu$Mol/l. Capillary zone electrophoresis (CZE) investigations was carried out using a system from Beckman. Peptides and enzymes were incubated in the capillary electrophoresis system at 37° C. using a 20 mM phosphate buffer pH 7.4. Decrease of substrate was determined by subsequent measurements of the same sample. Separation was carried out using a 0.1 M phosphate buffer pH 2.5, a 50 $\mu$m*30 cm fused silica capillary and 16 kV constant voltage. Peptides were detected at 200 nm. Substrate concentrations were calculated from the height of the peptide peaks. For determination of kinetic constants the degradation velocity from at least 4 substrate concentrations were determined and fitted according the Michaelis-Menten equation using Graphit 4.0.

Results

Figure 12:
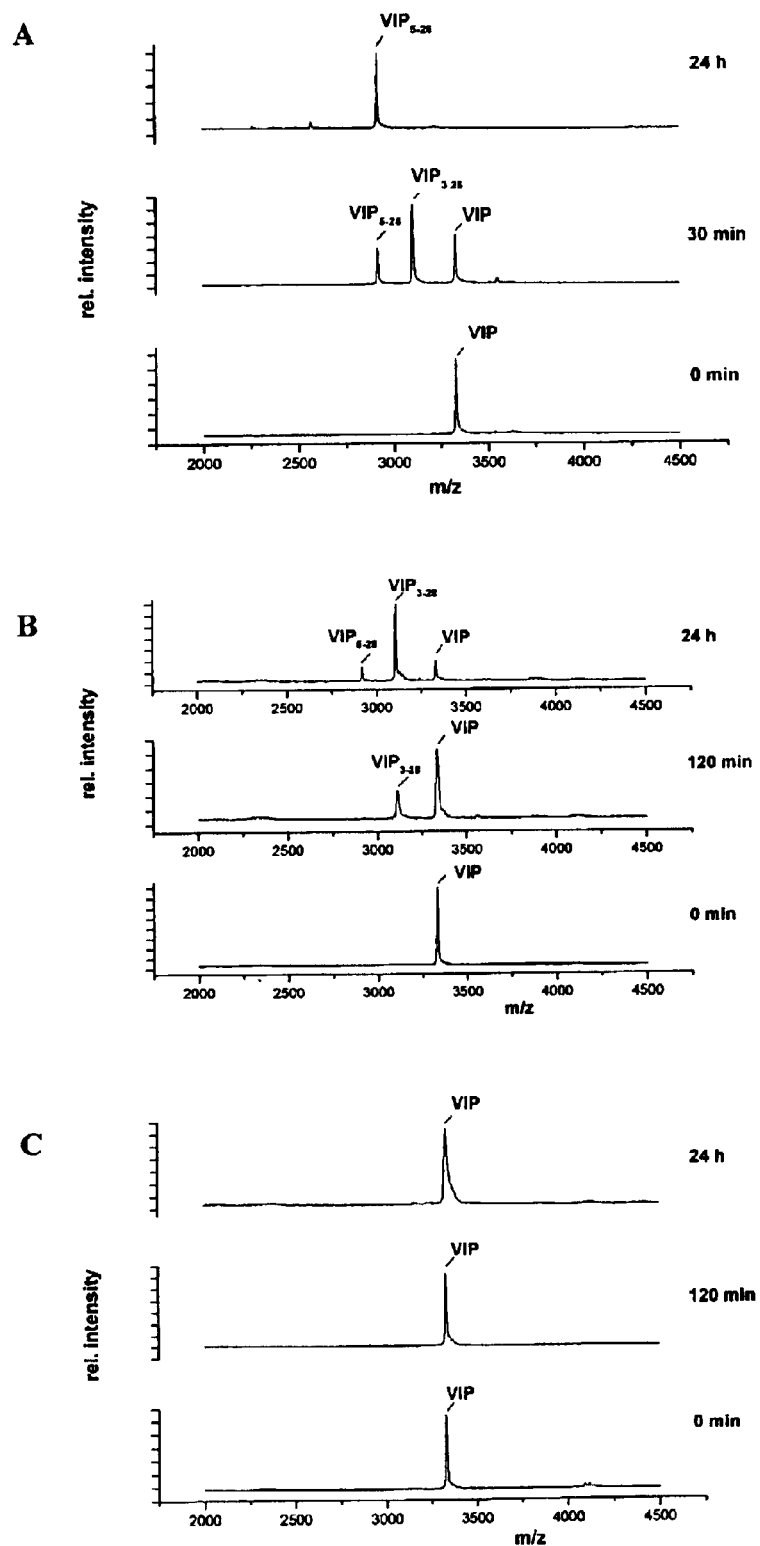
FIG. 12 shows MALDI-TOF mass spectra of the proteolytic processing of vasoactive intestinale peptide (VIP) by porcine kidney DP IV (A), human serum (B) and human serum, treated with the specific DP IV-inhibitor isoleucyl thiazolidine hemifumarate.
Figure 13:
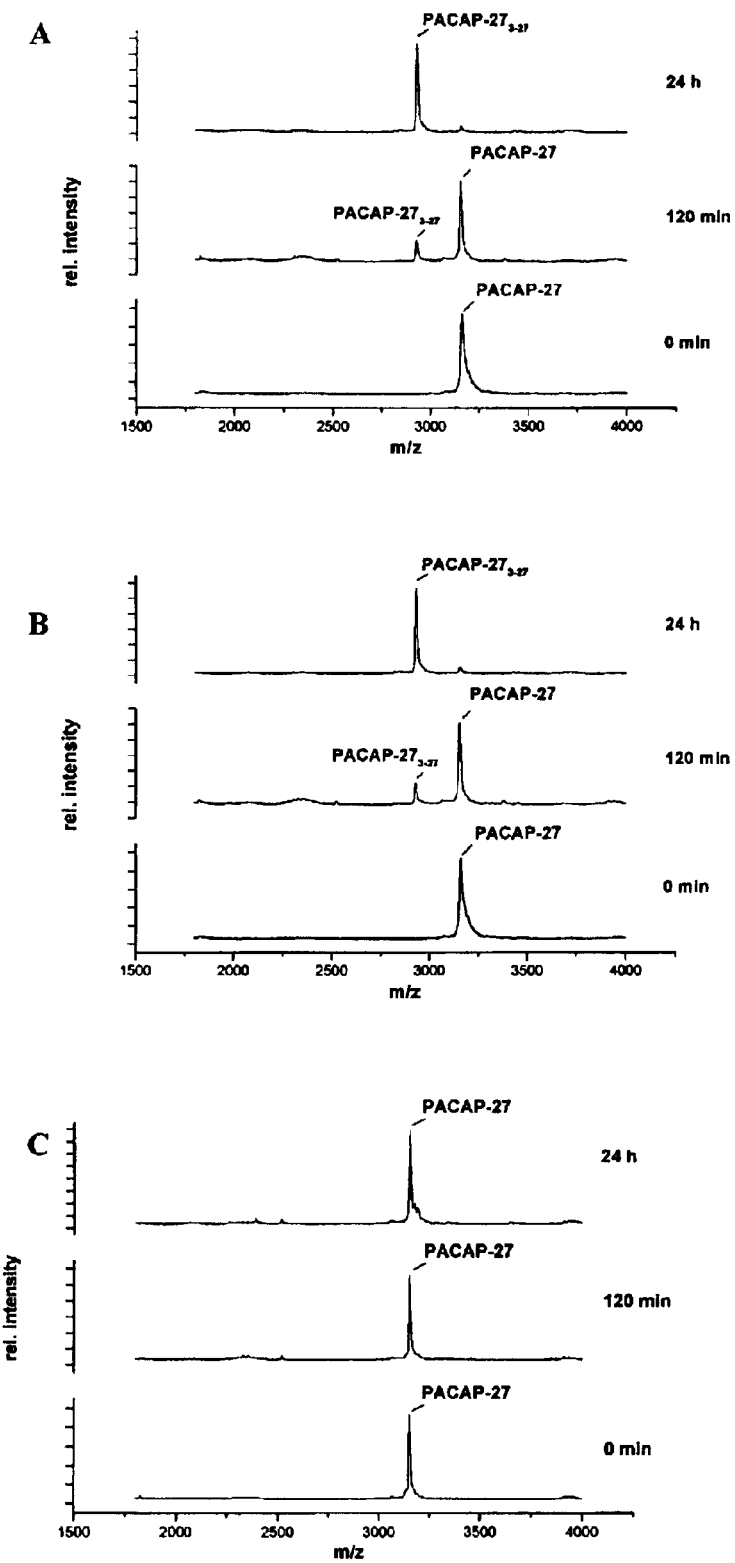
FIG. 13 shows MALDI-TOF mass spectra of the proteolytic processing of pituitary adenylate cyclase activating polypeptide 27 (PACAP 27) by porcine kidney DP IV (A), human serum (B) and human serum, treated with the specific DP IV-inhibitor P32/98.
Figure 14:
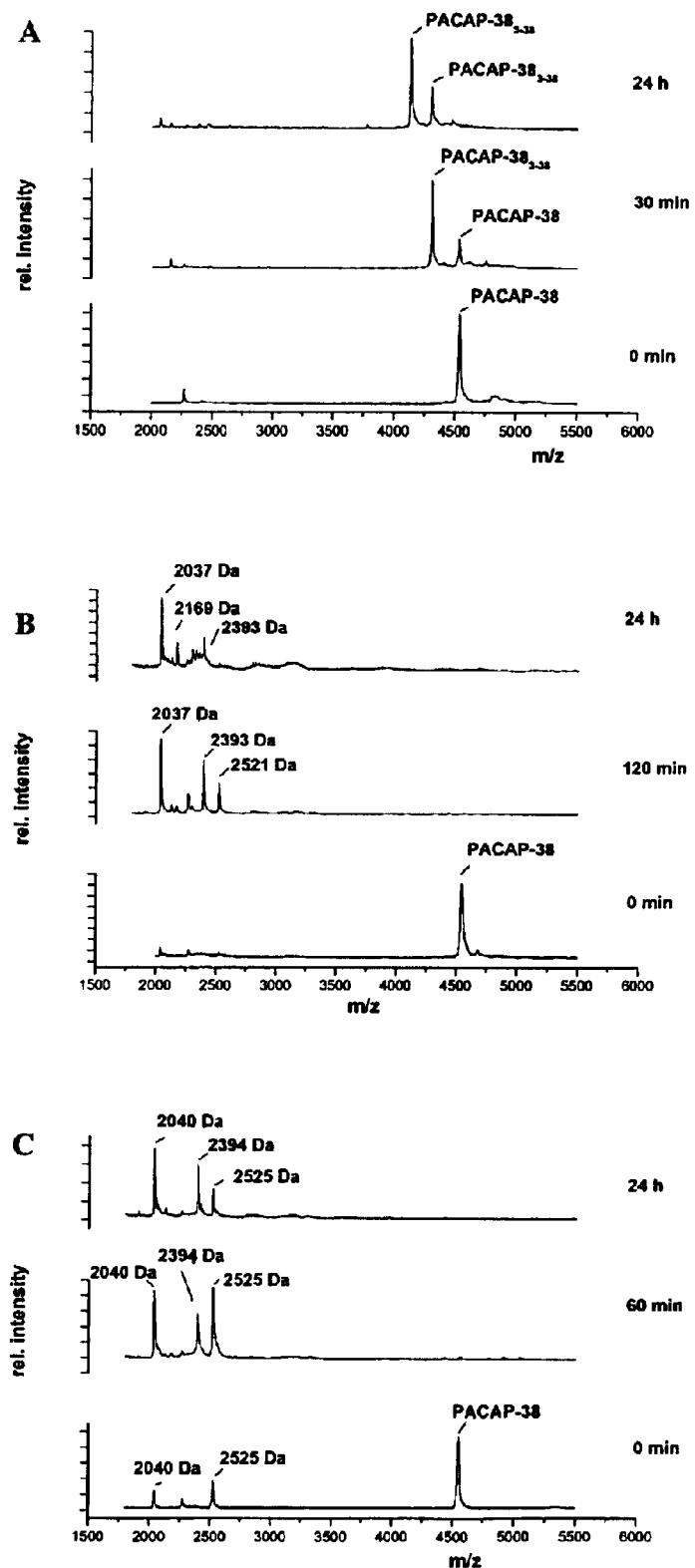
FIG. 14 shows MALDI-TOF mass spectra of the proteolytic processing of pituitary adenylate cyclase activating polypeptide 38 (PACAP 38) by porcine kidney DP IV (A), human serum (B) and human serum, treated with the specific DP IV-inhibitor P32/98.

Table 5 summarizes the results of proteolytic processing studies of gastrointestinal peptides analyzed by MALDI-TOF mass spectrometry (FIGS. 12–14) and capillary electrophoresis.

The evaluations of the mass spectra allowed a differentiation between the rates of cleavages under standard conditions and the determination of the substrate specificity (table 5). In addition, previously neglected substrate specificity (cleavage after Ser or Gly) were detected and confirmed. Hydrolysis in human plasma could be blocked by the dipeptidyl peptidase IV inhibitor isoleucyl thiazolidine hemifumarate.

TABLE 5

Qualitative analysis of the processing of selected gastrointestinal peptides by DP IV

| Peptide | N-terminal sequences | Cleavage, porcine DP IV | | Cleavage, human plasma + P32/98 |
|---|---|---|---|---|
| | | MALDI-TOF | $K_m$ ($\mu$M) $k_{cat}/K_m$ ($s^{-1}$ * $M^{-1}$) by CZE | CLEAVAGE, HUMAN PLASMA | |
| Growth-hormone releasing factor (GRF) | YADAVFTNS | ++++ | | ++++ | ø |
| Gastrin releasing peptide (GRP) | VPLPAGGGT | ++++ | | ++++ | ø |
| Pituitary adenylate cyclase activating polypeptide 27 (PACAP27) | HSDGIFTDS | ++ | | + | ø |
| Pituitary adenylate cyclase activating polypeptide 38 (PACAP38) | HSDGIFTDS | +++ | | immediate degradation in plasma results different fragments | inmediate degradation in plasma results different fragments |
| Secretin | HSDGTFTSE | +++ | | + | ø |
| Peptide histidin methionine (PHM) | HADGVFTSD | ++ | 35 1.3 e-9 | +++ | ø |
| Cholecystokinin (CCK21) | LAPSGNVSM. | – | | ++ Post-leucine cleavage by aminopeptidase followed by DP IV-catalyzed hydrolysis results CCK (4-21) in plasma | slow unspecific degradation by aminopeptidases |
| Vasoactive intestinale peptide (VIP) | HSDAVFTDN | +++ | | ++ | ø |
| Somatostatin 14 | AGCKNFWKT | ++ | 42 4.2e-6 | not determined | not determined |
| Somatostatin 28 | SANSNPAMA. | +++ | 6 7.9e-8 | not determined | not determined |
| Exendin-3 | HSDGTFTSD | + | | not determined | not determined |
| Exendin-4 | HGEGTFTSD | ++ | | not determined | not determined |
| Glucagon-like | HAEGTFTSD | +++ | | +++ | ø |

TABLE 5-continued

Qualitative analysis of the processing of selected gastrointestinal peptides by DP IV

| Peptide | N-terminal sequences | Cleavage, porcine DP IV | | * CLEAVAGE, HUMAN PLASMA | Cleavage, human plasma + P32/98 |
|---|---|---|---|---|---|
| | | MALDI-TOF | $K_m$ ($\mu$M) $k_{cat}/K_m$ (s$^{-1}$ M$^{-1}$) by CZE | | |
| peptide-1 Gastric inhibitory peptide | YAETFISDY | +++ | | +++ | ∅ |
| Glucagon | HSQGTFTS | ++ | 4 2.0e-5 | + | ∅ |

Discussion

Investigations performed on an acute scale (18–20, 29) do not exploit the potential benefits of long-term incretin effects such as the enhancement of β-cell glucose sensitivity and the stimulation of β-cell mitogenesis, differentiation, and insulin biosynthesis. It is one important embodiment of the present invention that long-term DP IV-inhibition arrested the progression of the fa/fa Zucker diabetic syndrome, and caused a progressive improvement in glucose tolerance, insulin sensitivity and β-cell glucose responsiveness.

Daily monitoring revealed a 12.5% decrease in body weight gain (4% reduction in final body weight) in the treated animals compared to untreated controls (FIG. 6A). Though not statistically significant, mean food intake in the treated animals averaged 0.4 g/day/rat (41 g/rat over the course of the study) less than those in the control group. It is possible that the cumulative 41 g/rat non-significant difference in food intake, apparent reduced desire for food or more rapid progress to satiety over the course of the experiment might partially account for the decreased weight gain in the treated animals.

Monitored on a bi-daily basis, morning and evening blood glucose values showed no significant response to the inhibitor treatment, a likely reflection of two points. First, the blood sampling times (0800 h and 1700 h) corresponded to post-absorptive and early feeding states respectively, with blood glucose values in the ranges 4.5–5.5 mM and 6.0–8.0 mM. In light of the hypothesized, glucose-dependent mechanism of action of the treatment, large decreases in glucose values would not be anticipated at these glycaemic levels. Secondly, both morning and evening blood samples were collected immediately prior to drug dosing, at times of minimum DP IV-inhibition where the potential for any acute therapeutic effects of the treatment were at a minimum. Both points are supported by the 24 hour profile shown in FIG. 7.

Figure 7:
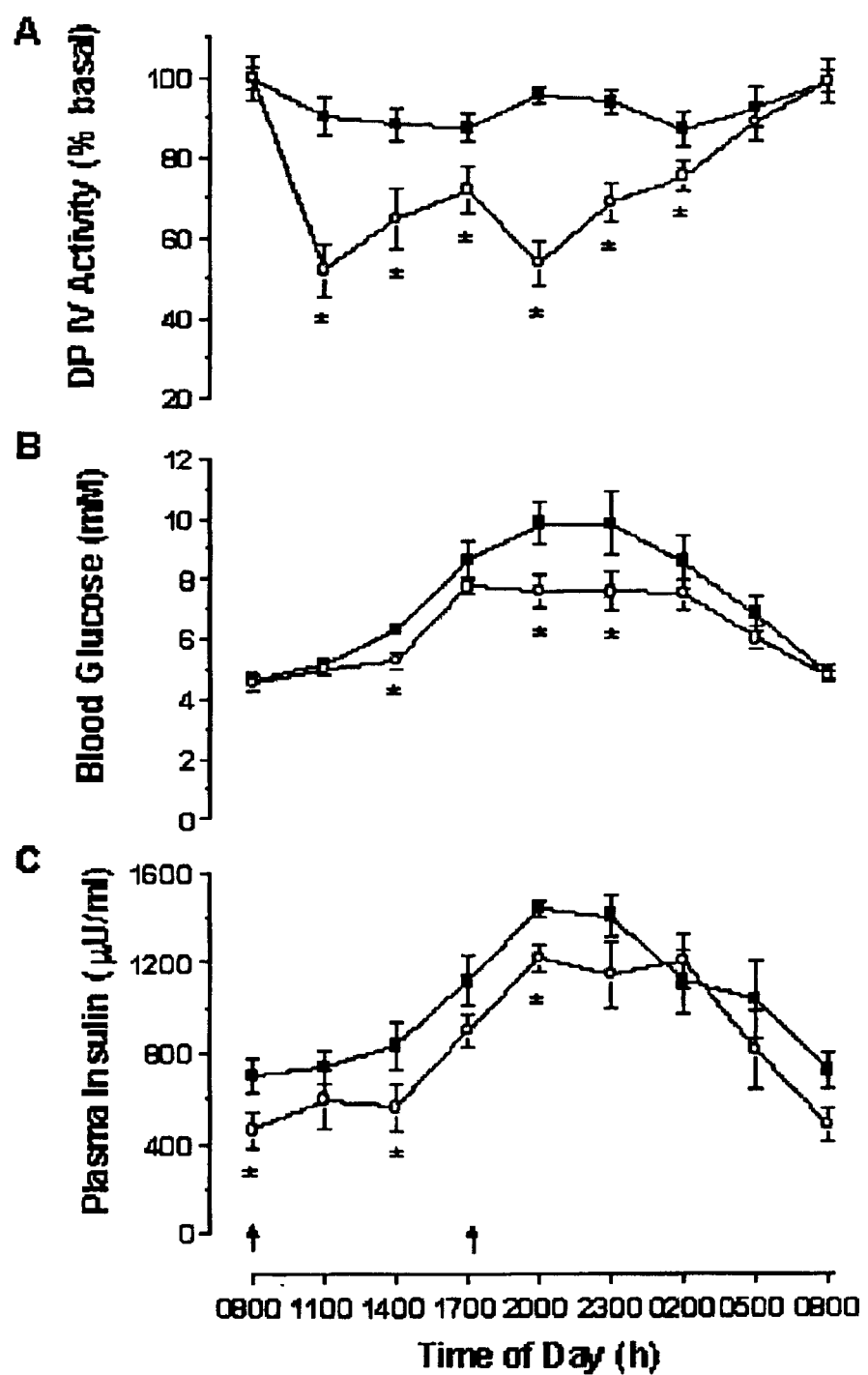
FIG. 7 shows a twenty-four hour profile of plasma DP IV-activity (A), blood glucose (B), and plasma insulin (C) levels in VDF rats after six weeks of treatment either with (open circles) or without (solid squares) the DP IV-inhibitor P32/98 (n=6). Treated animals were administered 10 mg/kg P32/98 twice daily as indicated by the arrows, while the control group received only the 1% cellulose injection vehicle. Statistical significance (p<0.05) is indicated by an asterisk.
Figure 8:
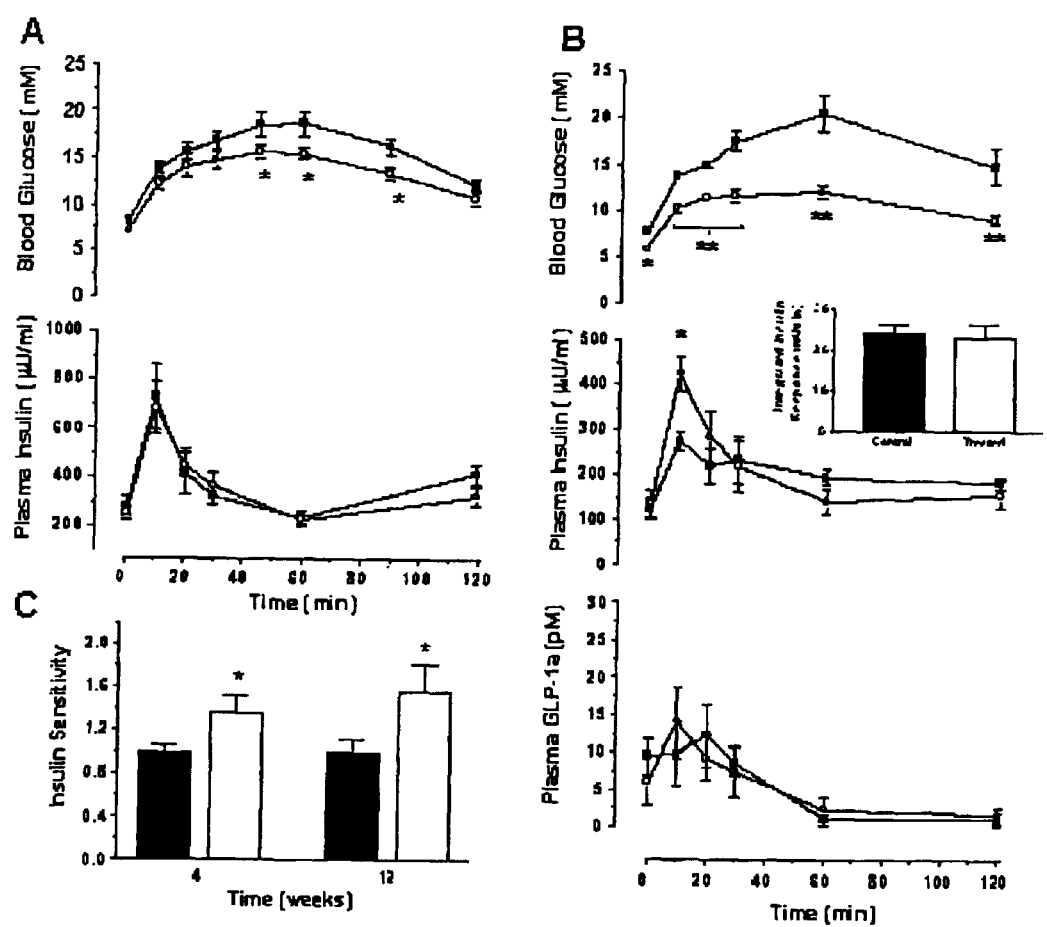
FIG. 8 shows oral glucose tolerance tests (OGTT) administered to both DP IV-inhibitor treated (open circles) and control (solid squares) VDF rats after four (A) and twelve (B) weeks of treatment (n=6). Blood glucose and plasma insulin measurements were performed in both series of tests, while the active fraction of plasma GLP-1 was also measured at twelve weeks. The inset in B shows the integrated plasma insulin responses for the twelve week OGTT. Statistical significance (p<0.05) is indicated by an asterisk. (C) Relative insulin sensitivity, control vs. treated, corresponding to the 4 and 12 week OGTTs shown in A and B.

The unaltered post-absorptive blood glucose values notwithstanding, DP IV-inhibitor treatment effectively reduced both prandial blood glucose and blood glucose responses to an OGTT (FIGS. 7&8). During the 24 hour profile the control animals exhibited a 105% rise in plasma insulin in response to a 5.2 mM increase in blood glucose, while the treated animals displayed a larger 160% insulin response to a much smaller glucose excursion (3.0 mM). While these differences were likely due, at least in part, to an acute increase in circulating incretin levels induced by P32/98, the pronounced early phase insulin peak exhibited during the OGTT was not (the OGTT took place after complete drug washout). The latter data were suggestive of not only of increased insulin sensitivity but also of enhanced β-cell glucose responsiveness. Ultimately, an increase in β-cell glucose responsiveness was clearly demonstrated through pancreas perfusion. Upon exposure to an elevated (8.8 mM) glucose perfusate, pancreata from the control animals showed an absence of first phase insulin release while those from the treated group exhibited an immediate, 3.2-fold insulin response (FIG. 10). The absence of early phase insulin release seen in the control group is characteristic of the VDF rat and is a hallmark of type 2 diabetes (21). Considering the lack of altered β-cell area or islet morphology, these data show that long-term treatment with a DP IV-inhibitor causes an improvement in the ability of the existing β-cell population to sense and respond to increases in glucose concentration.

Elevated fasting blood glucose in the face of hyperinsulinemia, and poor clearance of an oral glucose load, respectively, are consistent with the hepatic and muscle insulin resistance described in the fa/fa Zucker rat. Findings of the present study show that DP IV-inhibitor inhibitor treatment at least partially corrected both of these metabolic deviations, suggesting improvements in both sites of insulin resistance. An increased glucose to insulin ratio evident during the post absorptive state of the 24 hour profile (FIG. 7) as well as fasting values of the 12 week OGTT (FIGS. 8&9) were consistent with a decrease in insulin resistance in the treated animals. The latter increase in insulin sensitivity was shown to be significant at both 4 and 12 weeks using the composite insulin sensitivity index of Matsuda and DeFronzo (24). This mathematical analysis was previously validated (with high correlation) against the euglycaemic hyperinsulinemic clamp technique, in 153 subjects with varying degrees of insulin resistance. The relative insulin sensitivity of the treated animals improved with each successive OGTT ultimately reaching a relative index score 1.56±0.26 times that of the control animals. The results of the 24 hour glucose/insulin/DP IV profile and the OGTT were corroborated by direct measurements of glucose uptake in soleus muscle strips which clearly demonstrated improved glucose uptake in both the non-stimulated and insulin-stimulated states (FIG. 11). Though somewhat controversial, both GIP and GLP-1 (and exendin-4) have been reported to increase muscle insulin sensitivity through the stimulation of glycogen synthesis and glucose uptake (32–35). Additionally, a number of whole animal studies using GLP-1 or related GLP-1 receptor agonists have observed similar improvements in glucose tolerance and insulin sensitivity. Young and associates showed that long-term administration of the GLP-1 agonist Exendin-4 causes glucose lowering, and insulin sensitizing effects in a number of diabetic animal models including the fa/fa Zucker rat (36). Also, a number of sub-chronic infusion studies have revealed improvements in glycaemic control, glucose tolerance and insulin sensitivity (37–39). However, the indirect contributions of a long-term improvement in glycemia, or long-term enhancement of a number of other DP IV substrates (in particular the insulin secretagogues vasoactive intestinal peptide, pituitary adenylyl cyclase-activating peptide (PACAP)(48), gastrin-releasing peptide and neuropeptide Y) over the course of the treatment lead to the improved metabolic conditions which are one aspect of the present invention.

Other aspects which result from the present invention include the ability to increase a mammal's β-cells' ability to secrete insulin or to increase differentiation of a mammal's pancreatic cells to β-cells by increasing the availability of islet cell growth hormones which are responsive to central and/or peripheral nervous stimulation but which are substantially unresponsive to acute changes in circulating nutrient levels in said mammal. PACAP (48) is one such hormone. The preferred methods will comprise orally administering a therapeutically effective dose of an inhibitor of DP IV. Such administrations have also been surprisingly discovered to decrease the rate of chronic weight gain and also to result in decreasing or reducing decreasing weight. Still another surprising and unexpected aspect of the present invention involves improving the sensitivity of muscles to insulin by chronically administering a therapeutically effective dose of an inhibitor of DP IV, most preferably orally. Yet another advantage of the present invention is the ability to reduce a mammal's desire for food by chronic oral administration of a therapeutically effective dose of an inhibitor of DP IV. Still yet another advantageous result of the present invention is the decreased time to reaching a state of satiety in a mammal following the initiation of food intake, an effect which results from the chronic oral administration of a therapeutically effective dose of an inhibitor of DP IV. As a result, one is able to decrease the level of obesity in a mammal by following such methods.

An important facet shared by the OGTT, the muscle glucose uptake and the pancreas perfusion protocols was that cessation of drug treatment occurred 18 hours prior to these experimental procedures. Any divergence between groups, therefore, reflected long-term, lasting changes in metabolic state, rather than an acute effect of the drug. Drug washout was confirmed by DP IV-activity measurements.

With regard to example 9, enzymatic hydrolysis of gastrointestinal peptides using purified porcine kidney DP IV as well as human plasma containing DP IV-activity was shown. Dipeptidyl Peptidase IV is capable to cleave peptides of the GRF family containing Ser or Gly in penultimate position, Substrate specificity could be confirmed in the presence of specific inhibitors for DP IV and DP IV-like enzymes. DP IV is responsible for inactivation of glucagon in vivo.

All publications cited herein are fully incorporated by reference.

What is claimed is:

1. A method for improving for improving β-cell capacity to secrete insulin in response to increased glucose levels comprising administering a therapeutically effective dose of a DP IV-inhibitor thereby increasing the availability of islet cell growth hormone to pancreatic cells wherein said islet cell growth hormone circulates at a level which is substantially unresponsive to acute changes in glucose level said DP IV-inhibitor comprises a dineptide compound selected from the group consisting of N-valyl prolyl, O-benzoyl hydroxylamine, alanyl pyrrolidine, L-allo-isoleucyl thiazolidine, L-allo-isoleucyl pyrrolidine, L-threo-isoleucyl thiazolidine, L-threo-isoleucyl pyrrolidine, asparaginyl pyrrolidine, asparaainyl thiazolidine, asparagyl pyrrolidine, asparagyl thiazolidine, glutamyl pyrrolidine, glutamyl thiazolidine, glutaminyl pyrrolidine, glutaminyl thiazolidine, histidyl pyrrolidine, histidyl thiazolidine, isoleucyl azitidine, valyl pyrrolidine and valyl thiazolidine, or a pharmaceutical acceptable salt thereof.

2. The method of claim 1 wherein said increasing step comprises potentiating the activity of said islet cell growth hormone.

3. The method of claim 2 wherein said islet cell growth hormone is PACAP.

4. The method of claim 1 wherein said administration comprises chronic oral administration.

5. The method of claim 1 wherein said step of increasing the availability of islet cell growth hormone to pancreatic cells promotes differentiation of said pancreatic cells to specialized cells of the islet of Langerhans.

6. The method of claim 2 wherein said potentiating step comprises repeated oral dosing of an inhibitor of DP IV.

7. The method of claim 1 wherein said inhibitor is a substrate for DP IV which competes with natural substrates for binding to said DP IV.

8. The method of claim 1 wherein said inhibitor further comprises a pharmaceutically acceptable carrier.

9. The method of claim 8 wherein said carrier comprises glucose.

10. A method for increasing a mammal's β-cells' ability to secrete insulin or differentiation of pancreatic cells to β-cells in a mammal comprising administering a therapeutically effective dose of an inhibitor of DP IV thereby increasing within said mammal the availability of islet cell growth hormones which are responsive to central and/or peripheral stimulation and substantially unresponsive to acute changes in circulating nutrient levels in said mammal wherein said DP IV-inhibitor comprises a dipeptide compound selected from the group consisting of N-valyl prolyl, O-benzoyl hydroxylamine, alanyl pyrrolidine, L-allo-isoleucyl thiazolidine, L-allo-isoleucyl pyrrolidine, L-threo-isoleucyl thiazolidine, L-threo-isoleucyl pyrrolidine, asparaginyl pyrrolidine, asparaginyl thiazolidine, asparagyl pyrrolidine, asparagyl thiazolidme, glutamyl pyrrolidine, glutamyl thiazolidine, glutaminyl pyrrolidine, glutaminyl thiazolidine, histidyl pyrrolidine, histidyl thiazolidine, isoleucyl azitidine, valyl pyrrolidine and valyl thiazolidine, or a pharmaceutical acceptable salt thereof.

11. The method of claim 10 comprising increasing the availability of PACAP.

* * * * *